United States Patent [19]

Mookherjee et al.

[11] Patent Number: 4,839,083
[45] Date of Patent: Jun. 13, 1989

[54] SCHIFF BASE REACTION PRODUCTS OF MIXTURES OF ALDEHYDES INCLUDING HELIONAL AND ALKYL ANTHRANILATES; DERIVATIVES THEREOF; AND ORGANOLEPTIC USES THEREOF

[75] Inventors: Braja D. Mookherjee, Holmdel; Robert W. Trenkle, Point Pleasant, both of N.J.; Nicholas Calderone, Laurel Hollow, N.Y.; Lisa Schreck, Tinton Falls; Keith P. Sands, Marlboro, both of N.J.

[73] Assignee: International Flavors & Fragrances Inc., New York, N.Y.

[21] Appl. No.: 164,503

[22] Filed: Mar. 4, 1988

Related U.S. Application Data

[63] Continuation-in-part of Ser. No. 114,247, Oct. 29, 1987, Pat. No. 4,775,720.

[51] Int. Cl.$^4$ .............................................. C11D 3/50
[52] U.S. Cl. ................... 252/174.11; 252/99; 252/102; 252/186.1; 252/549; 512/81; 512/19; 512/20; 512/23; 512/25
[58] Field of Search ............... 252/95, 99, 102, 135, 252/186.1, 549; 560/19, 35, 48; 512/8, 19, 20, 23, 25; 549/466; 568/446, 377

[56] References Cited

U.S. PATENT DOCUMENTS 4,774,225 9/1987 Giraudi ........................... 512/9
4,775,720 10/1988 Mookherjee et al. ........ 252/174.11

FOREIGN PATENT DOCUMENTS 153212 7/1987 Japan.

Primary Examiner—A. Lionel Clingman
Assistant Examiner—Hoa Van Le
Attorney, Agent, or Firm—Arthur L. Liberman

[57] ABSTRACT

Described are schiff base reaction products of alkyl anthranilates having the structure:

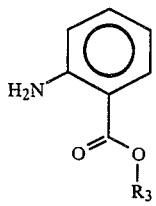

wherein $R_3$ represents methyl or ethyl; helional having the structure:

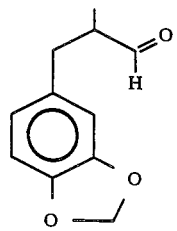

and aldehydes having the generic structure:

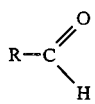

wherein R represents a hydrocarbyl or hydroxy hydrocarbyl moiety including the aldehydes:
(a) pinoacetaldehyde having the structure:

(Abstract continued on next page.)

(b) pinoisobutyraldehyde having the structure:

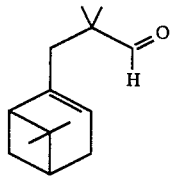

and (c) lyral, a mixture of compounds having the structures:

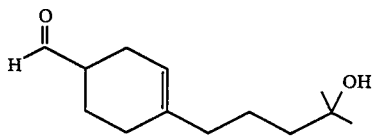

and

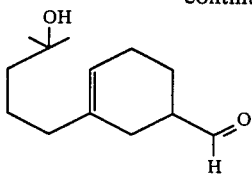

and derivatives there and organoleptic uses thereof in augmenting or enhancing the aroma or taste of consumable materials including perfume compositions, colognes, perfumed articles, foodstuffs, chewing gums and beverages. Also described are processes for deodorizing articles and compositions of matter and axillary regions of mammalian species comprising the step of treating such articles, compositions or axillary regions with schiff base reaction products of such alkyl anthranilates and helional; or schiff base reaction products of such alkyl anthranilates, helional and aldehydes defined according to the structure:

17 Claims, 19 Drawing Sheets

FIG. 1 — GC-SPECTRAL SCAN FOR EXAMPLE I.

FIG. 4 GC-SPECTRAL SCAN FOR EXAMPLE II.

MASS SPECTRUM FOR EXAMPLE II.

FIG.6 MASS SPECTRUM FOR EXAMPLE II.

MASS SPECTRUM FOR EXAMPLE IV(A).

FIG. 13 — MASS SPECTRUM FOR EXAMPLE IV(A).

MASS SPECTRUM FOR EXAMPLE IV(A).

MASS SPECTRUM FOR EXAMPLE IV(A).

FIG.17 MASS SPECTRUM FOR EXAMPLE IV(A).

SCHIFF BASE REACTION PRODUCTS OF MIXTURES OF ALDEHYDES INCLUDING HELIONAL AND ALKYL ANTHRANILATES; DERIVATIVES THEREOF; AND ORGANOLEPTIC USES THEREOF

This application is a continuation-in-part of application for U.S. Pat. No. 114,247 filed on Oct. 29, 1987, now U.S. Pat. No. 4,775,720.

BACKGROUND OF THE INVENTION

Our invention relates to reaction products which are schiff bases of aldehydes and alkyl anthranilates and uses thereof in (i) augmenting or enhancing the aroma or taste of perfume compositions, colognes, perfumed articles, foodstuffs, chewing gums and beverages and (ii) effecting deodorization of skin surfaces, compositions and articles having undesirable or aesthetically displeasing aromas.

Inexpensive chemical compositions of matter which can provide green, orange flower, fruity, ozoney, sweet, anisic, melony, herbaceous, balsamic, walnut and floral aromas with grape, fruity, green, flower, anisic, ozoney, piney, meloney and lemony topnotes are highly desirable in the art of perfumery. Many of the natural materials which provide such fragrances and contribute desired nuances to perfumery compositions as well as perfumed articles including solid or liquid anionic, cationic, nonionic or zwitterionic detergents, fabric softener compositions and fabric softener articles are high in cost, vary in quality from one batch to another and/or are generally subject to the usual variations of natural products.

By the same token, materials which can provide intense floral, oriental, citrus, lemony, meloney, watermelon, green and concord grape aromas with watermelon, floral, oriental, citrus, lemony, meloney, green, raspberry and concord grape tastes are highly useful and well known in the art of flavoring for foodstuffs, toothpastes, chewing gums, medicinal products and chewing tobaccos. Many of the natural materials which provide such flavor nuances and contribute desired nuances to flavoring compositions are high in cost, vary in quality from one batch to another and/or are generally subject to the usual variations of natural products.

There is, accordingly, a continuing effort to find synthetic materials which will replace, enhance or augment the essential flavor and fragrance notes provided by natural essential oils or compositions thereof. Unfortunately, many of the synthetic materials either have the desired nuances only to a relatively small degree or else contribute undesirable or unwanted odor to the compositions. The search for materials which provide, for example, a more refined grape-like flavor or more refined lemon flavor or more refined watermelon flavor, for example, has been difficult and relatively costly in the areas of both natural products and synthetic products. By the same token, the search for materials which can provide a more refined green, orange flower, fruity, ozoney, sweet, anisic, melony, herbaceous, balsamic, walnut and floral aromas with grape, fruity, green, flower, anisic, ozoney, piney, meloney and lemony topnotes has been difficult and relatively costly in the areas of both natural perfumery products and synthetic perfumery products.

Artificial flavoring agents for foodstuffs have received increasing attention for many years. For many years such food flavoring agents have been preferred over natural flavoring agents at least in part due to their diminished costs and their reproducible flavor qualities. For example, natural food flavoring agents such as extracts, concentrates and the like are often subject to wide variations due to changes in quality and type and treatment of the raw materials. Such variations can be reflected in the end products and result in unfavorable flavor characteristics in the end product. Additionally, the presence of the natural product in the ultimate food may be undesirable because of increasing tendency to spoil. This is particularly troublesome in food and food uses where such products as dips, soups, chips, sausages, gravies and desserts and the like are apt to be stored prior to use.

Even more desirable are products that can serve to substitute for difficult-to-obtain natural perfumery oils and, at the same time, substitute for natural flavoring ingredients in foodstuffs, chewing gums, medicinal products, toothpastes and chewing tobaccos.

Reaction products of carbonyl-containing compounds and amine-containing compounds are well known in the art of flavoring and in the art of of perfumery. Thus, U.S. Pat. No. 4,618,501 issued on Oct. 21, 1986 discloses the flavoring of foodstuffs with alpha,-beta-keto-amines and states that an alpha,beta-keto-amine having a nutty corn, cereal aroma may be used for flavoring compositions for foods having the structure:

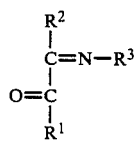

wherein $R_1$, $R_2$ and $R_3$ are selected from the group consisting of a saturated or unsaturated alkyl straight or branched chain hydrocarbons having from 1-3 carbon atoms.

U.S. Pat. No. 3,625,710 issued on Dec. 7, 1971 discloses the use of aldimines as chocolate-like flavors which aldimines are resulting from the reaction product of amines and aldehydes, for example, N-isobutylidenefurfurylamine, N-isopentylidenefurfurylamine, N-isopentylideneisopentylamine.

Schiff bases are also well known in the art of perfumery. Thus, for example, Chemical Abstracts Volume 103, 1985, No. 123134z (Abstract of Japan Kokai No. 60/78951 discloses the use in perfumery of compounds having the structure:

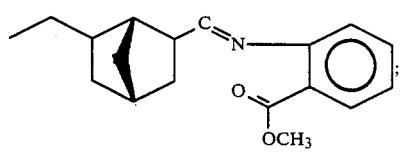

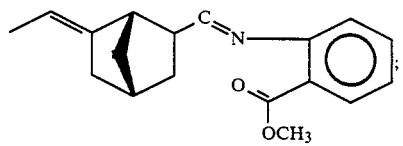

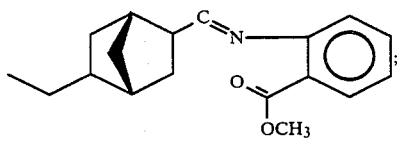

and

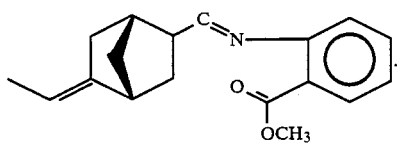

The book "Flavor & Fragrance Materials-1987" published by Allured Publishing Corporation, P.O. Box 318, Wheaton, Ill. 60189-0318 discloses on page 154 the commercial availability of the following schiff bases:
Methyl anthranilate and amyl cinnamic aldehyde;
Methyl anthranilate and hydroxy citronellal;
Methyl anthranilate and lilial;
Methyl anthranilate and anisic aldehyde;
Methyl anthranilate and decanal;
Methyl anthranilate and lyral;
Methyl anthranilate and iso-nonylaldehyde;
Methyl anthranilate and phenylacetaldehyde;
Schiff bases are also known to be useful as intermediates in producing other fragrance materials. Thus, U.S. Pat. No. 3,898,283 issued on Aug. 5, 1975 discloses novel schiff base intermediates used in producing 4 or 5 phenylpentenals having the structure:

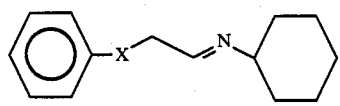

wherein X is a moiety selected from the group consisting of:

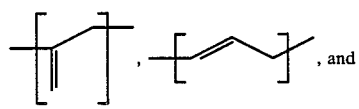

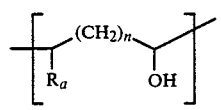

and wehrein $R_a$ is hydrogen or methyl.

Nothing in the prior art however discloses the novel reaction products or reaction product mixtures of our invention having unobvious, unexpected and advantageous organoleptic properties.

Indeed, nothing in the prior art is indicative of the novel schiff base reaction products of our invention having deodorizing properties that is, having a deodorant value of 0.50 up to 3.5 as measured by the deodorant value test described in U.S. Pat. No. 4,304,679 incorporated by reference herein or having a Lipoxidase-inhibiting capacity of at least 50% and a Malodour reduction value of from 0.25 up to 3 as measured by the Malodour reduction value test disclosed in U.S. Pat. No. 4,663,068 incorporated by reference herein.

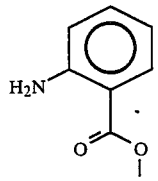

and helional having the structures:

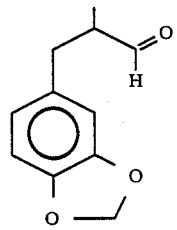

containing a mixture of the compounds having the structures:

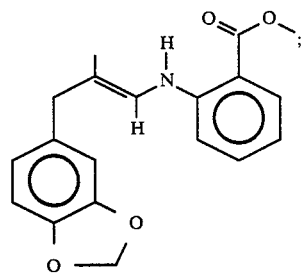

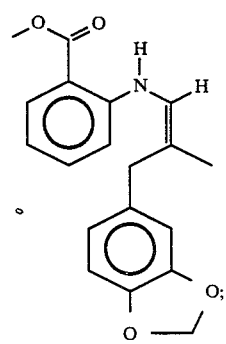

and

-continued

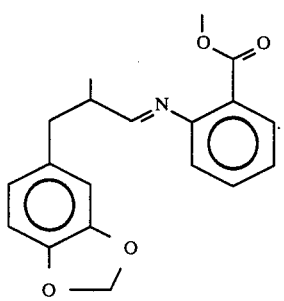

Figure 2:
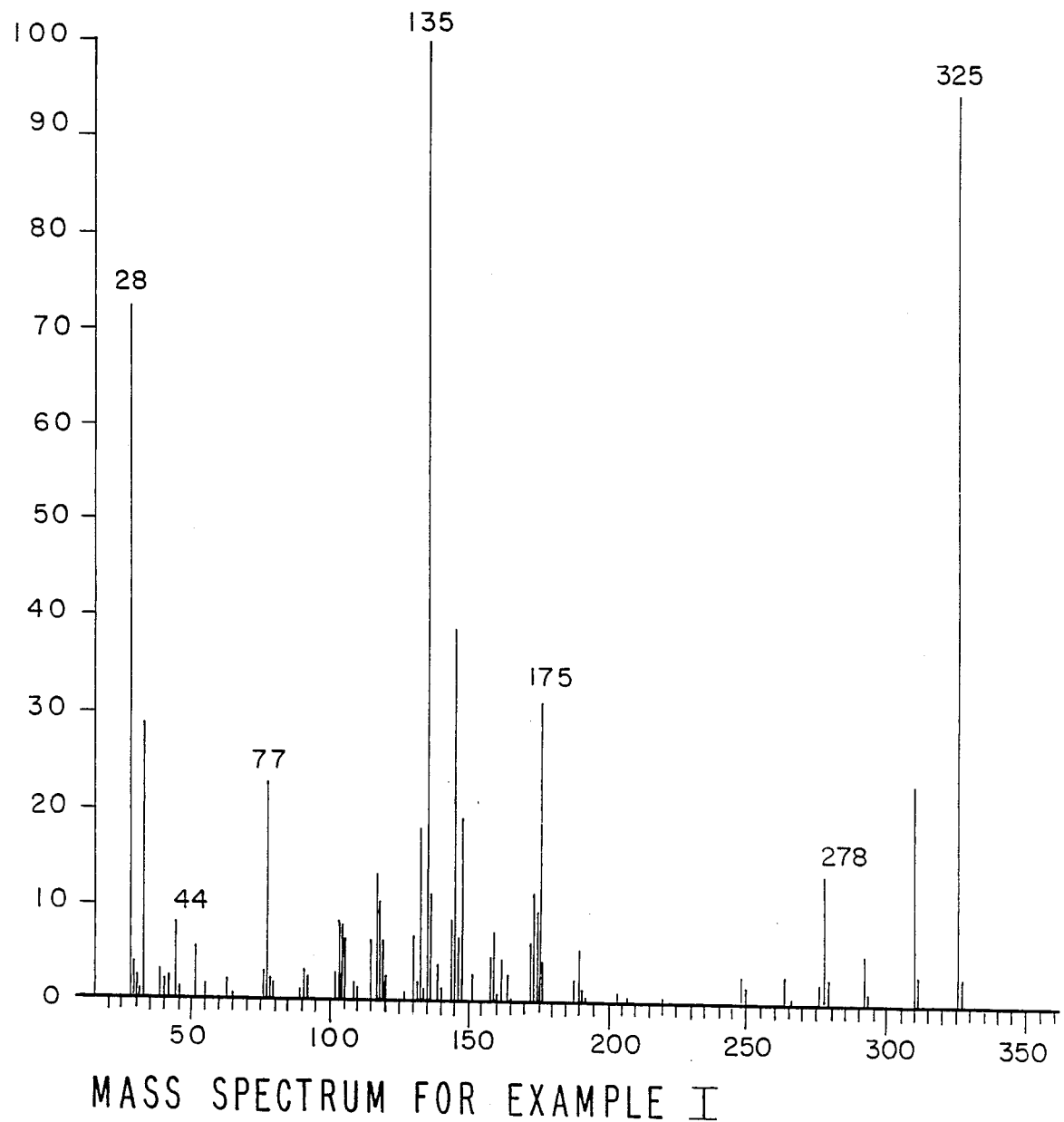

FIG. 2 is the mass spectrum for the compounds having the structures:

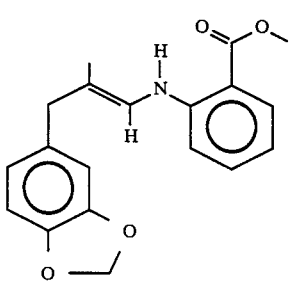

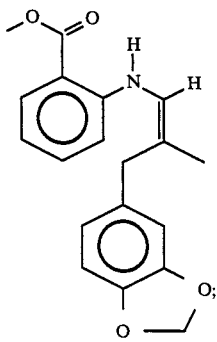

and

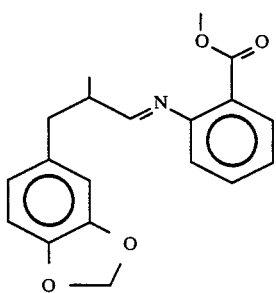

prepared according to Example I.

Figure 3:
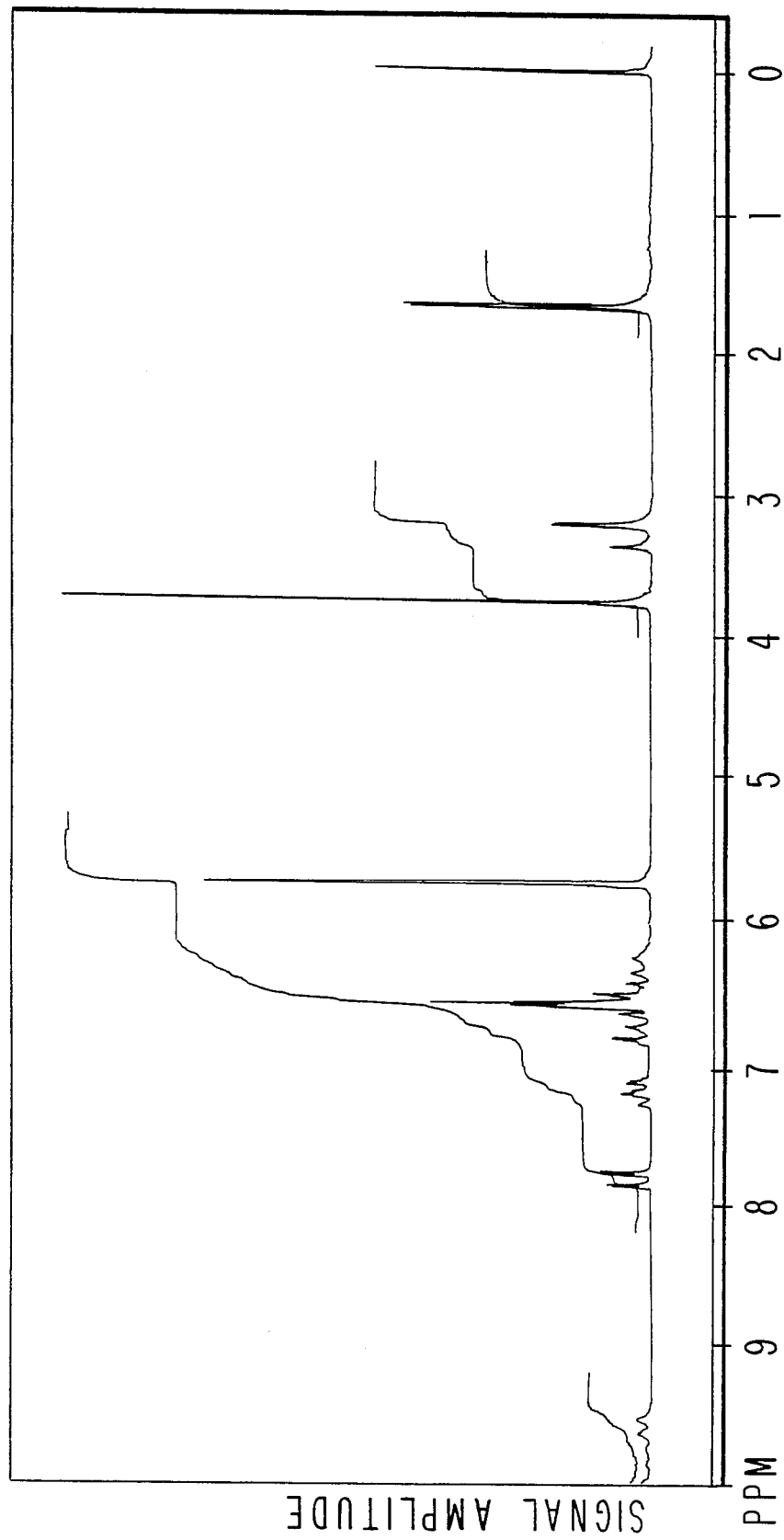

FIG. 3 is the NMR spectrum for the compound having the structure:

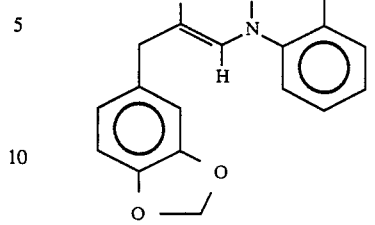

prepared according to Example I.

Figure 4:
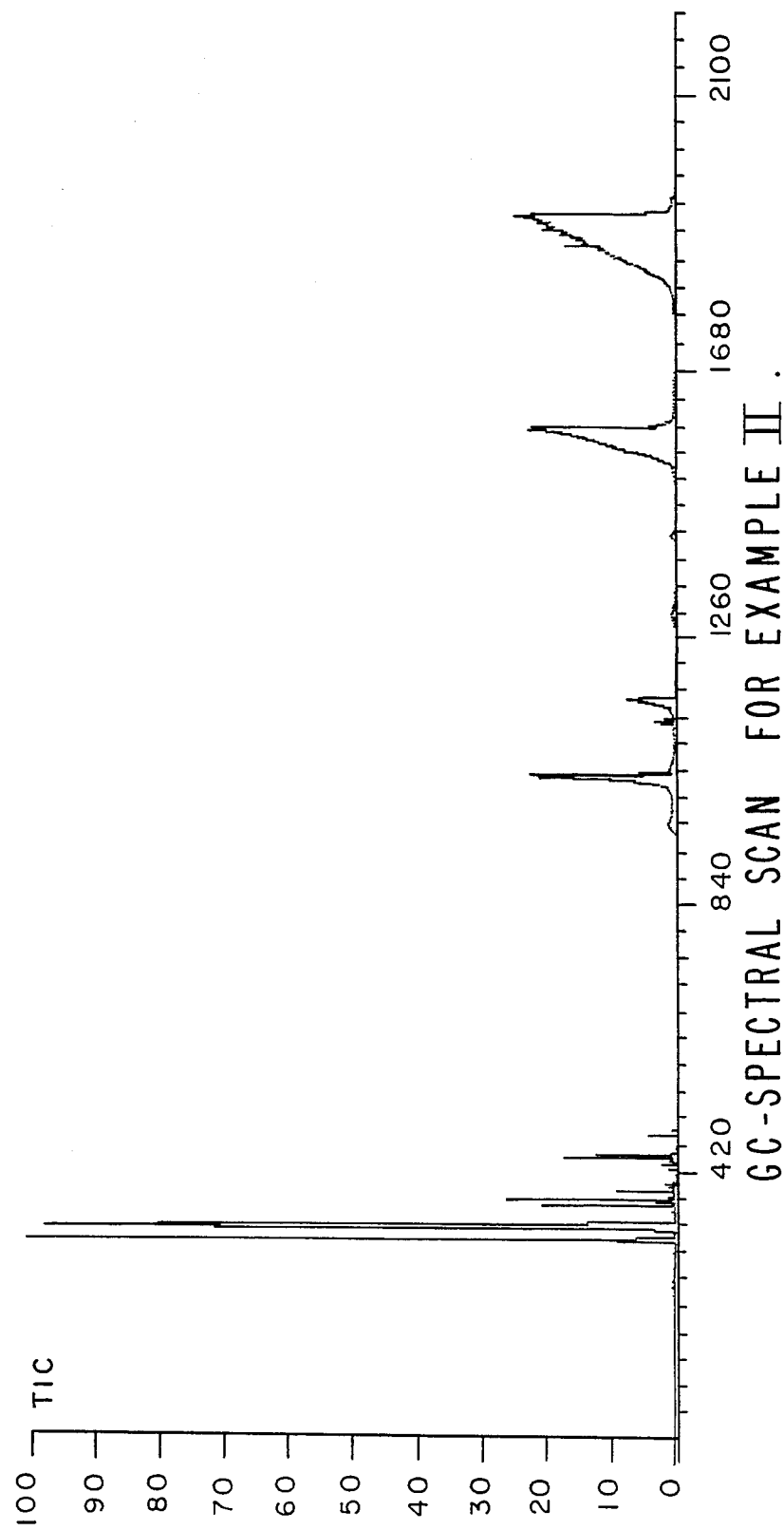

FIG. 4 is the GC-spectral scan for the reaction product of Example II which is a reaction product of pino acetaldehyde having the structure:

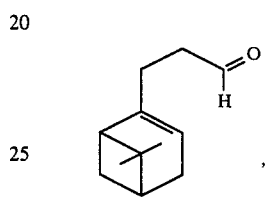

helional having the structure:

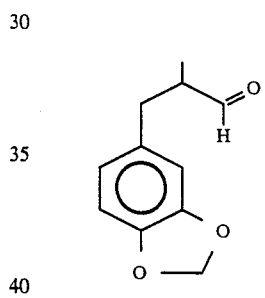

and methyl anthranilate having the structure:

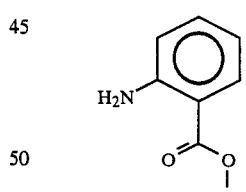

and which contains the compounds having the structures:

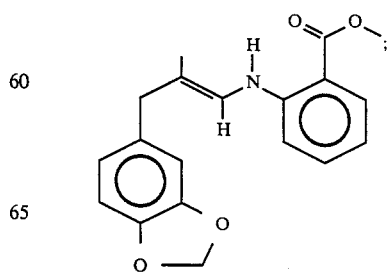

-continued

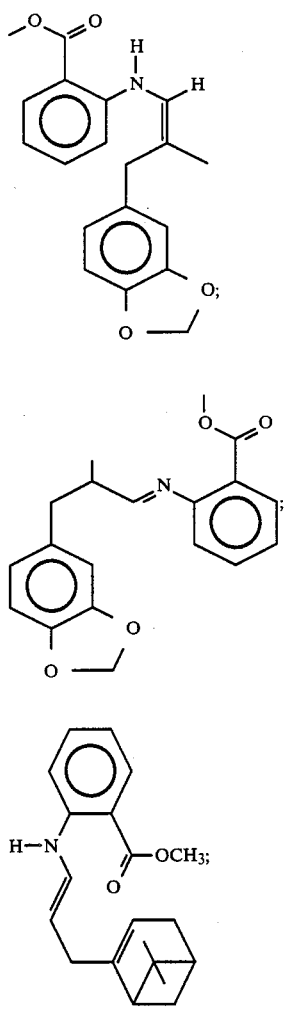

Figure 5:
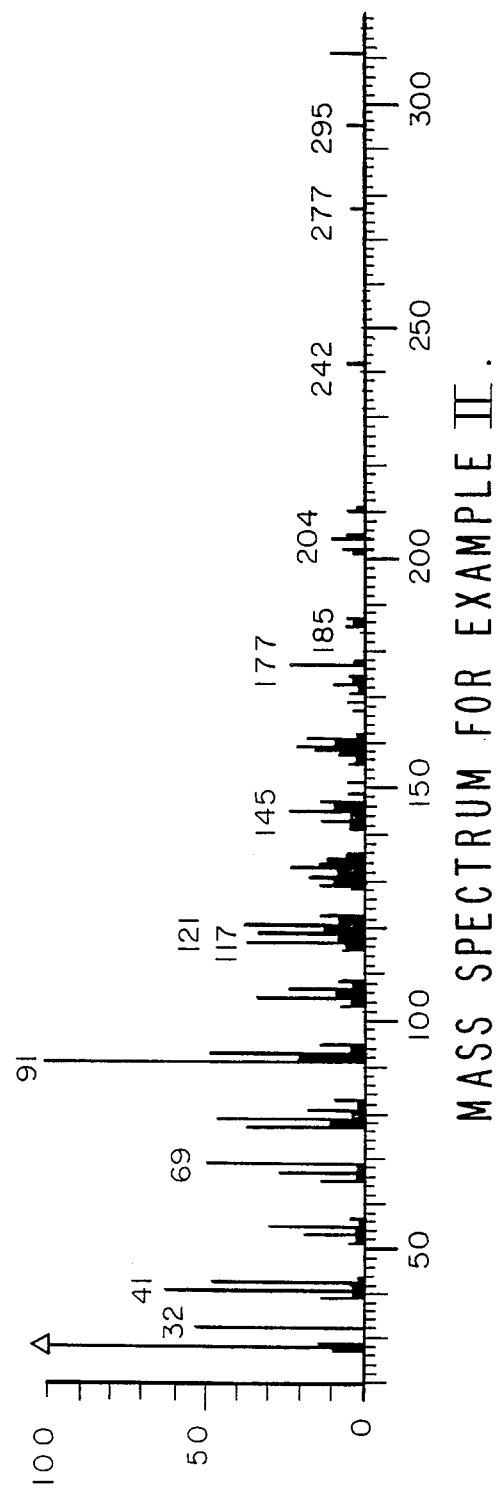

FIG. 5 is the mass spectrum for a compound having one of the structures:

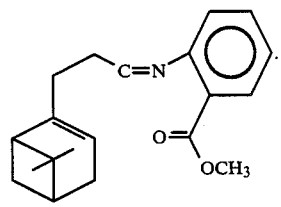

or

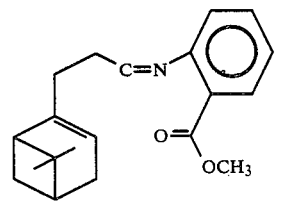

-continued

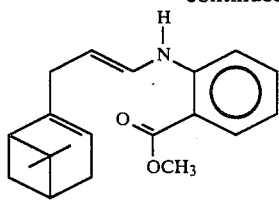

prepared according to Example II.

Figure 6:
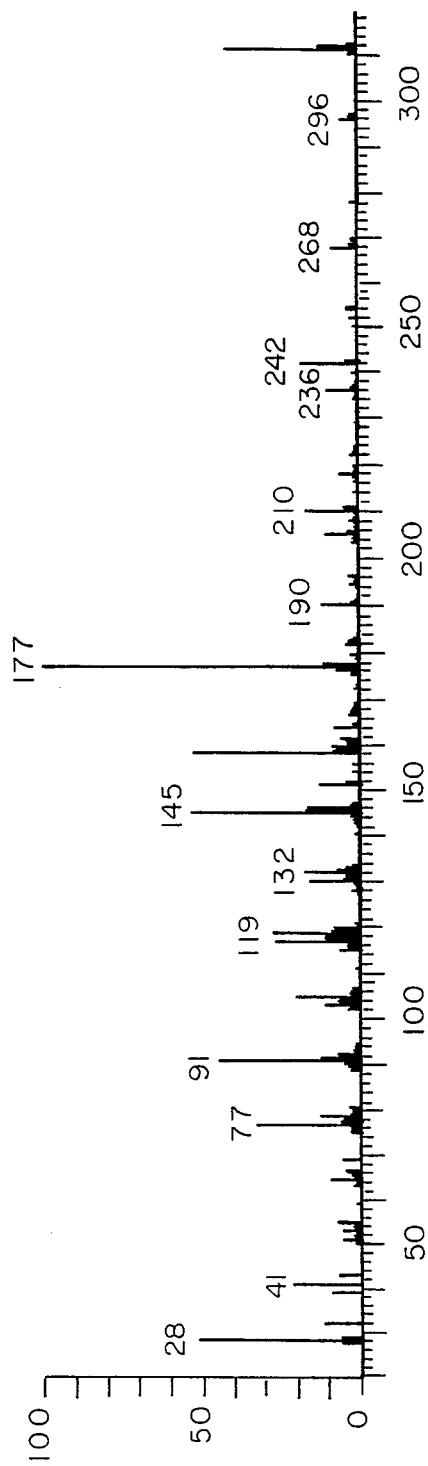

FIG. 6 is the mass spectrum of a compound having one of the structures:

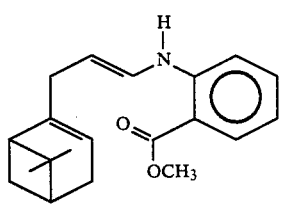

or

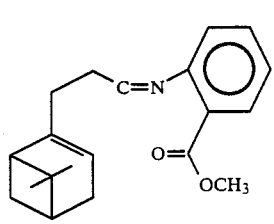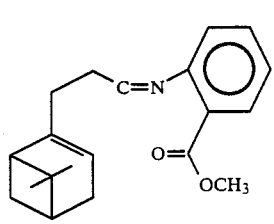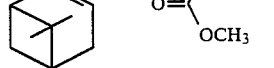

prepared according to Example II.

Figure 7:
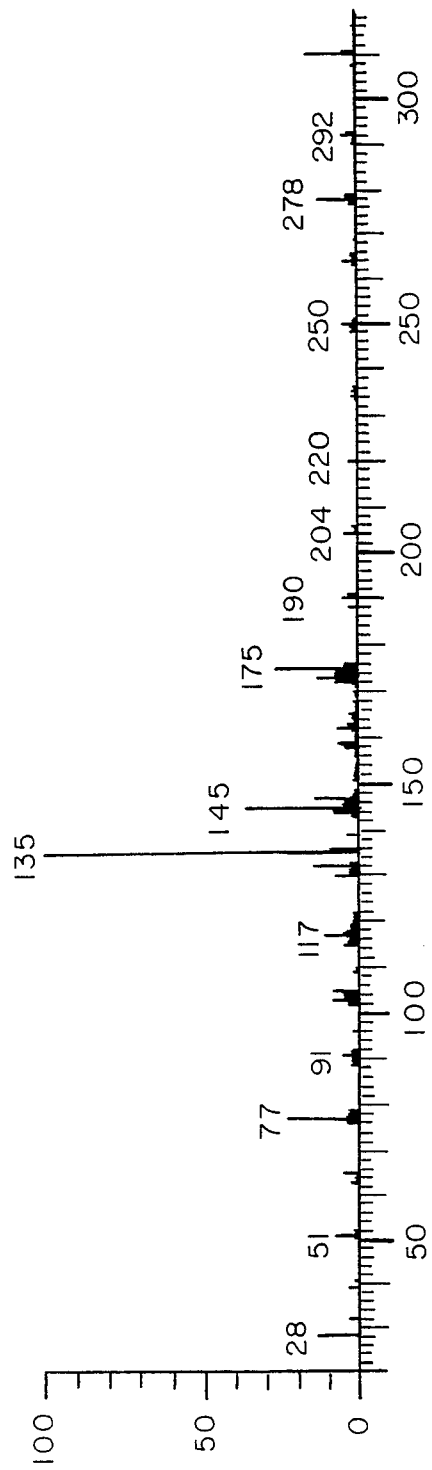

FIG. 7 is the mass spectrum of one of the compounds having one of the structures:

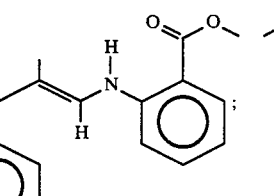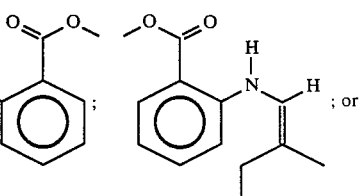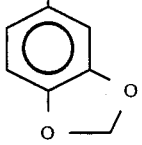

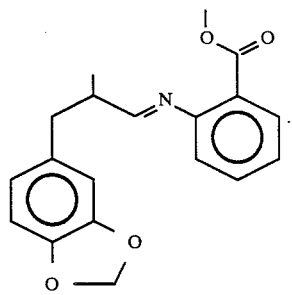

Figure 8:
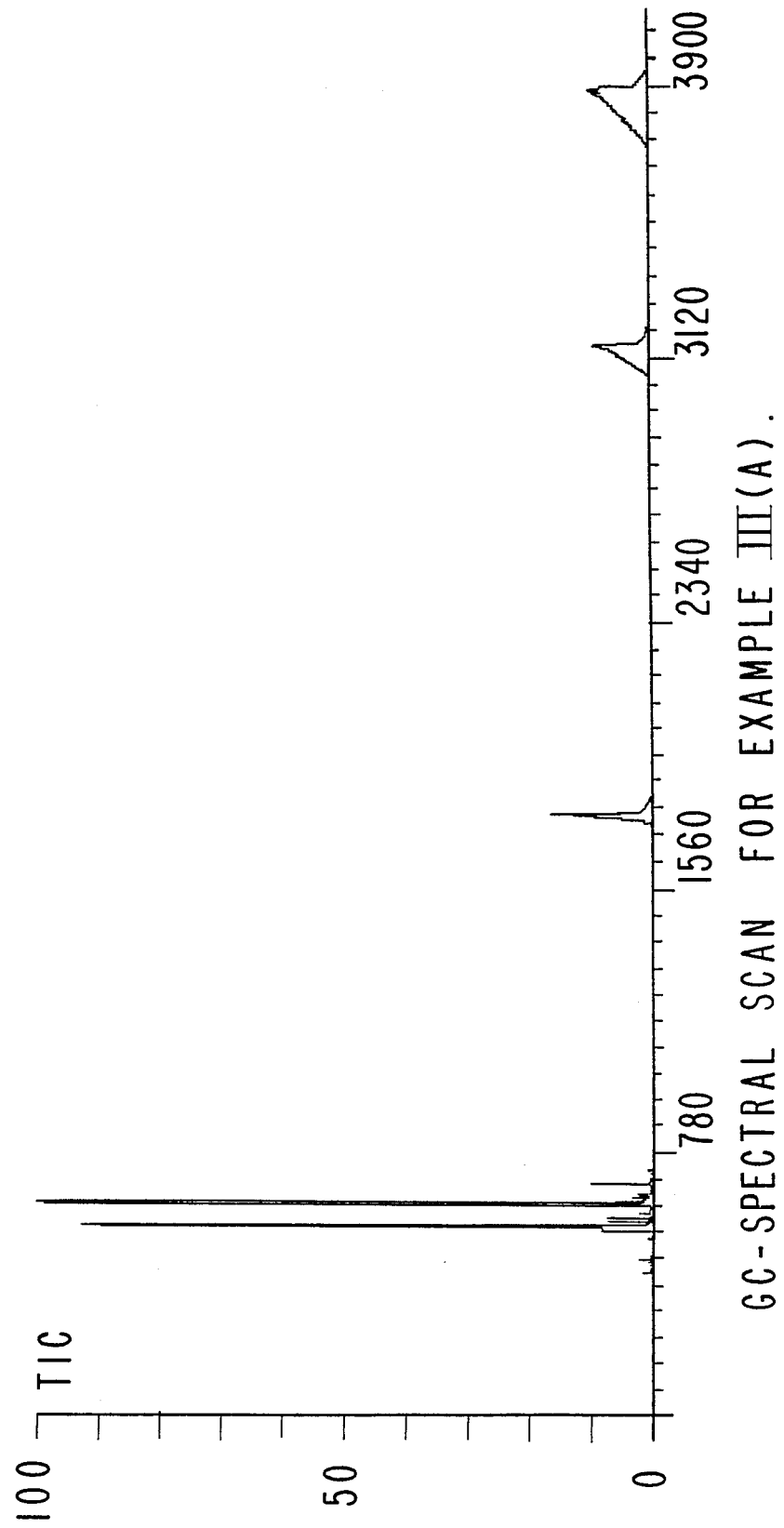

FIG. 8 is the GC spectral scan for the mixture of compounds produced according to Example III(A), a reaction product of pino isobutyraldehyde having the structure:

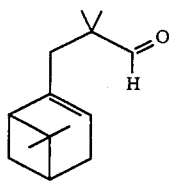

helional having the structure:

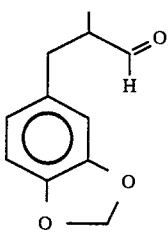

and methyl anthranilate having the structure:

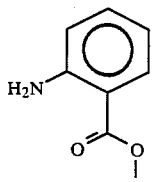

which are compounds having the structures:

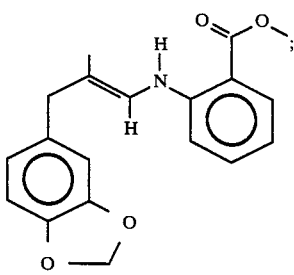

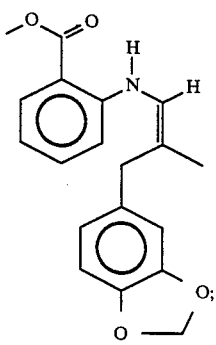

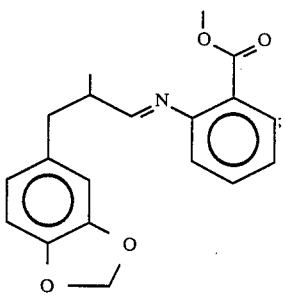

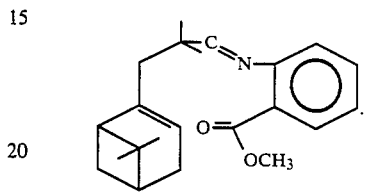

Figure 9:
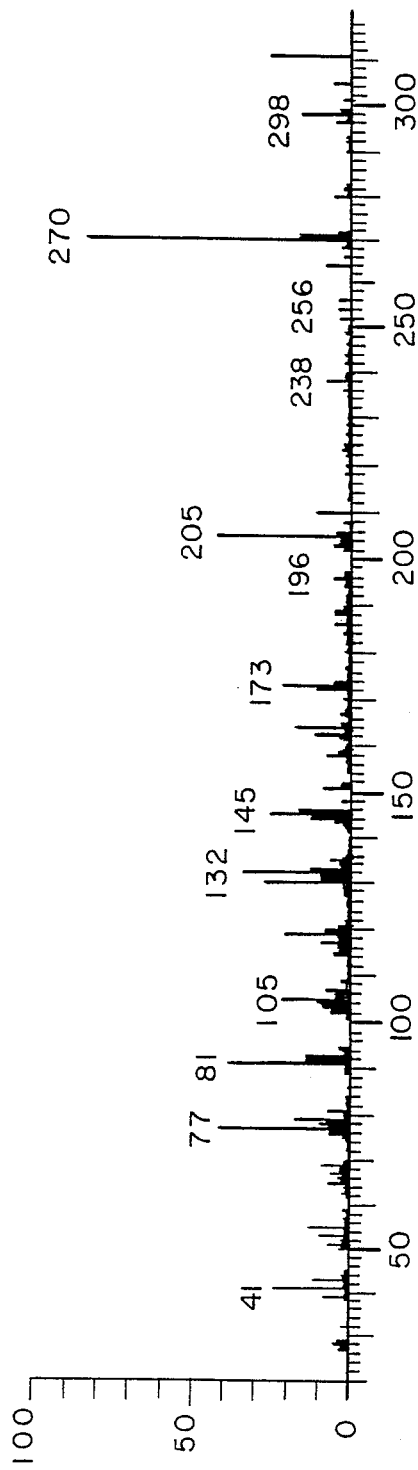

FIG. 9 is the mass spectrum for the compound having the structure:

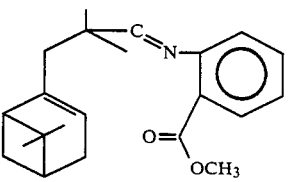

prepared according to Example III(A).

Figure 10:
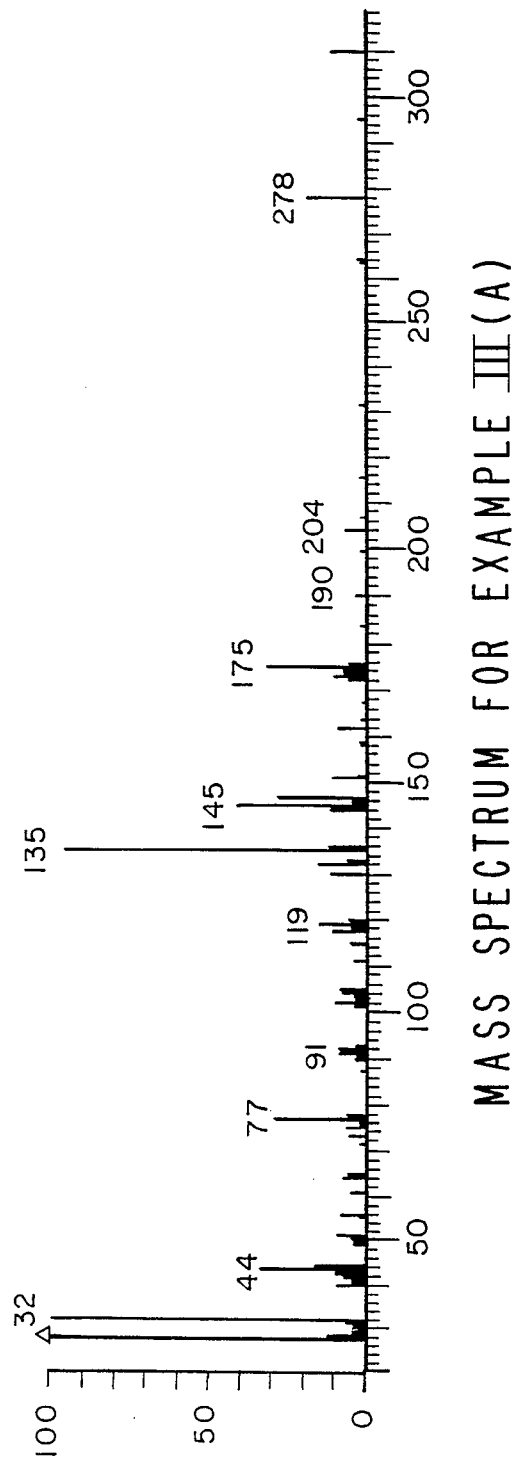

FIG. 10 is the mass spectrum for one of the compounds having one of the structures:

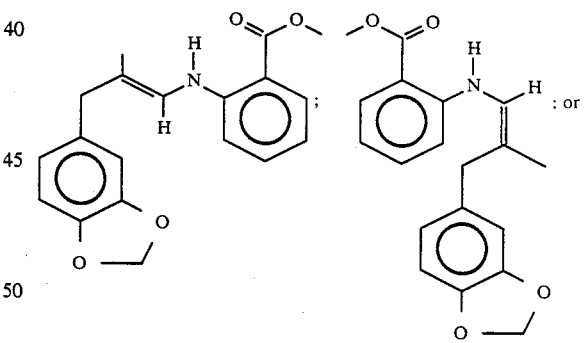

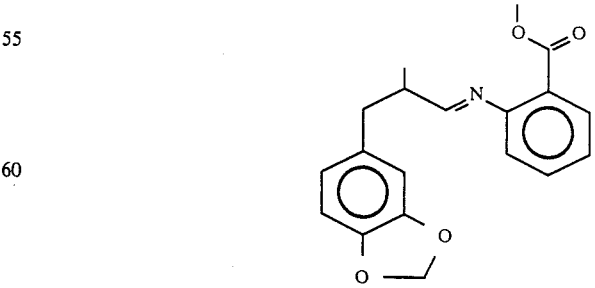

produced according to Example III(A).

Figure 11:
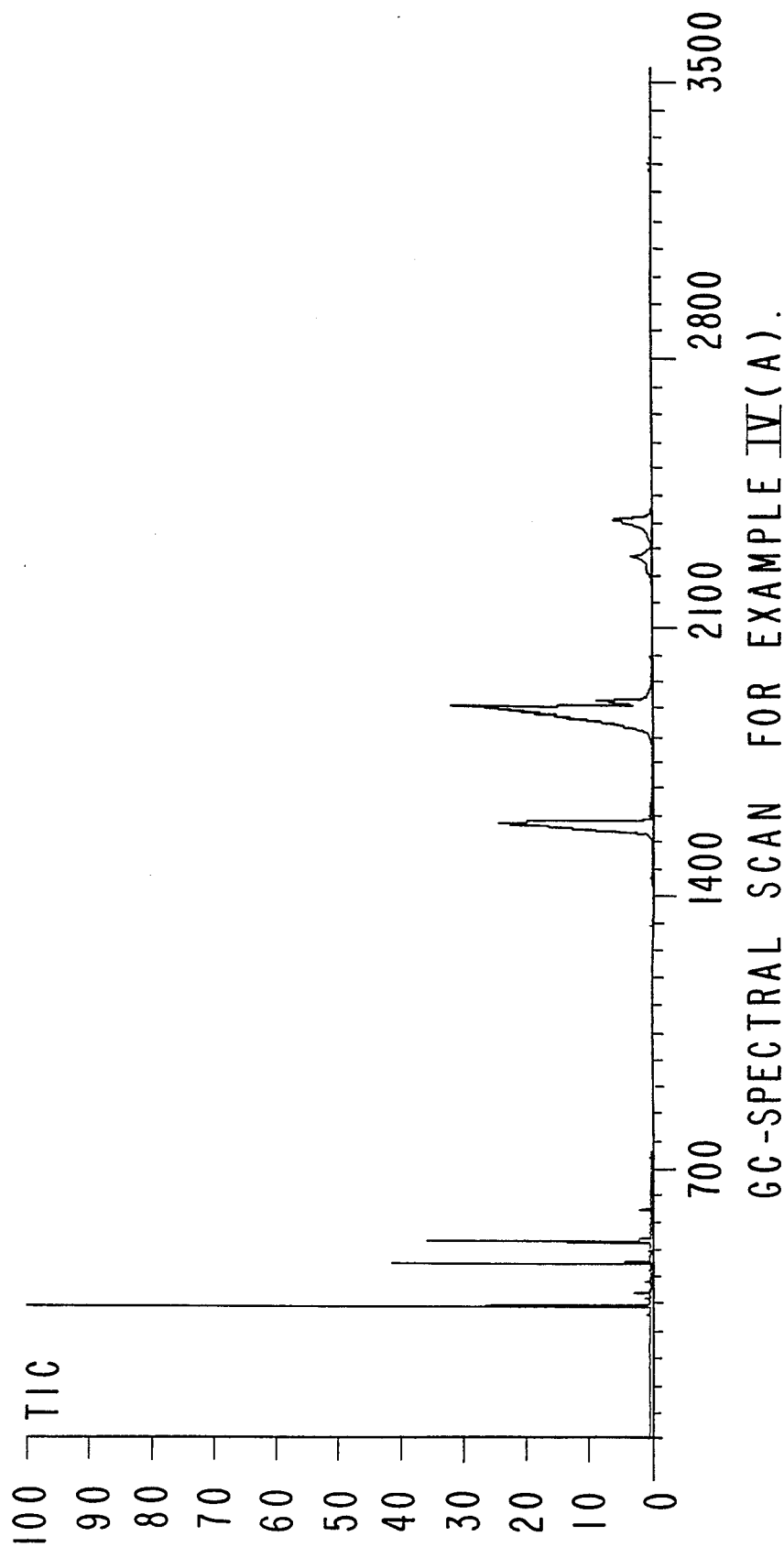

FIG. 11 is the GC spectral scan for the reaction product produced according to Example IV(A), the reaction product of lyral (a mixture of compounds having the structures:

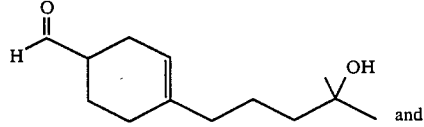

and

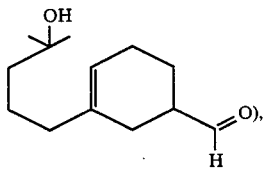

), helional the compound having the structure:

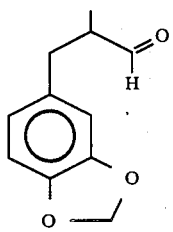

and methyl anthranilate having the structure:

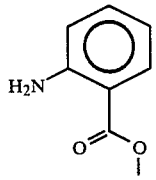

the reaction product being a mixture of compounds having the structures:

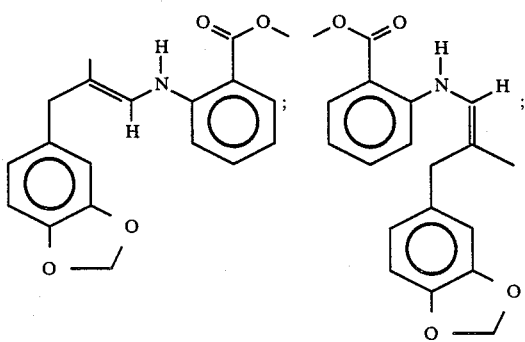

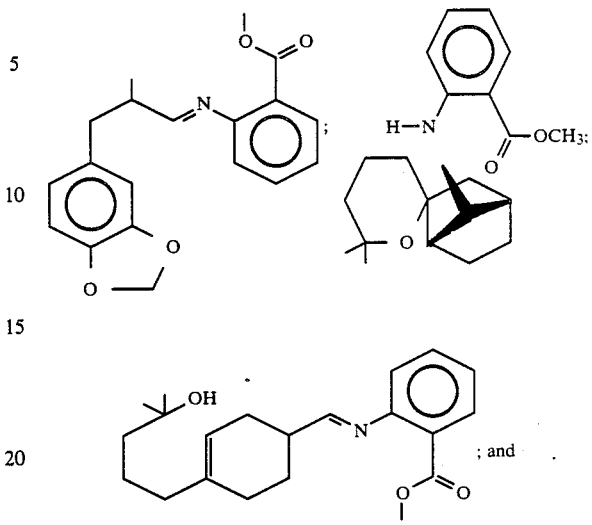

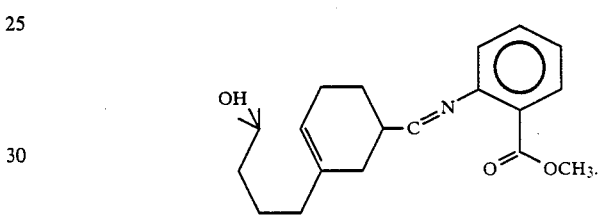

Figure 12:
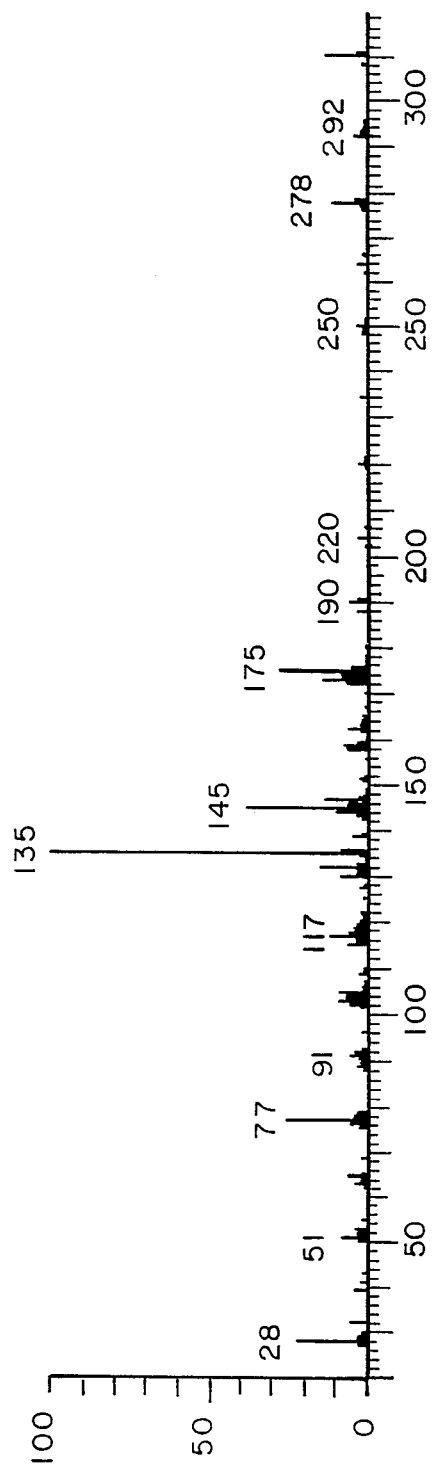

FIG. 12 is the mass spectrum for one of the compounds having the structures:

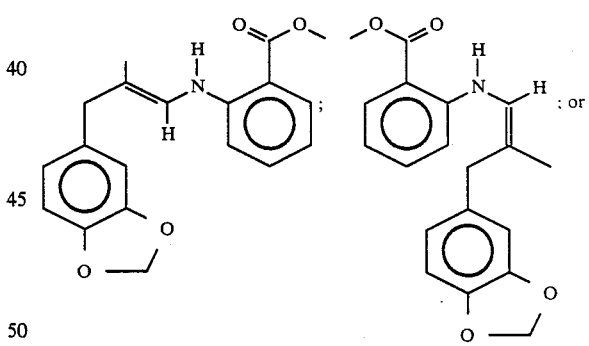

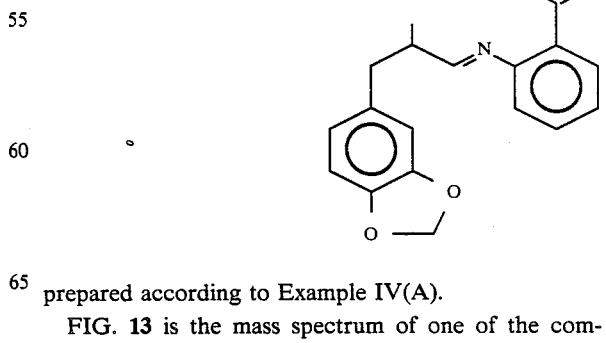

prepared according to Example IV(A).

Figure 13:
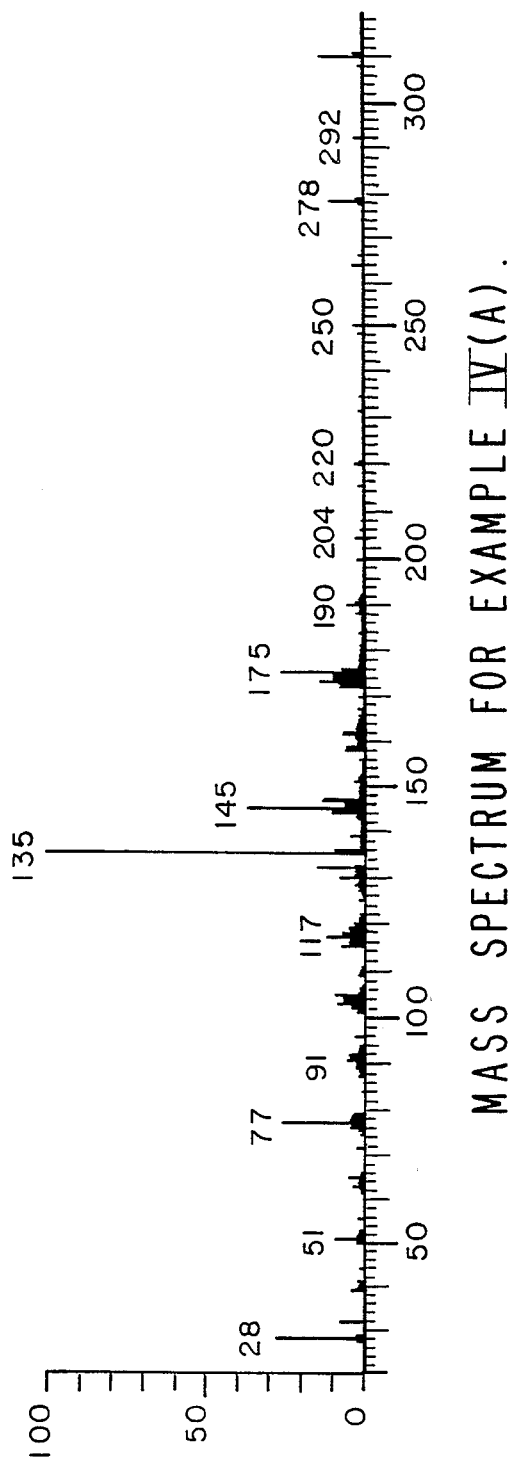

FIG. 13 is the mass spectrum of one of the compounds having one of the structures:

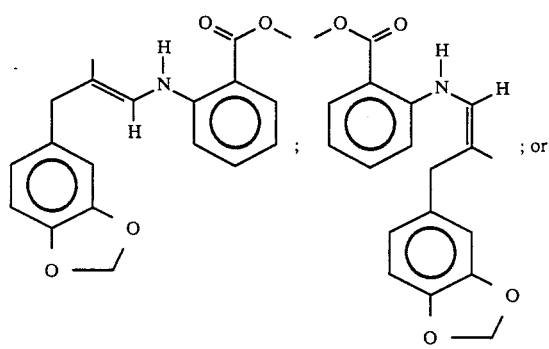

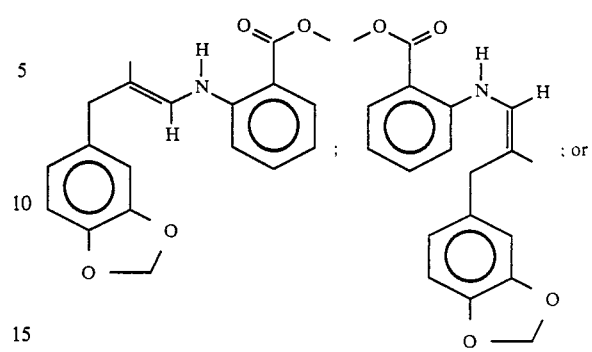

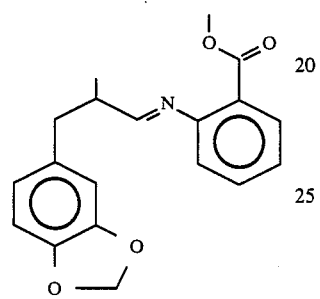

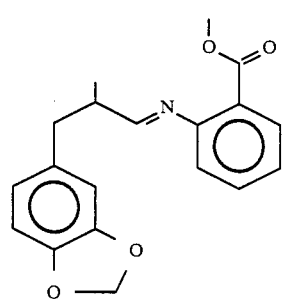

prepared according to Example IV(A).

Figure 14:
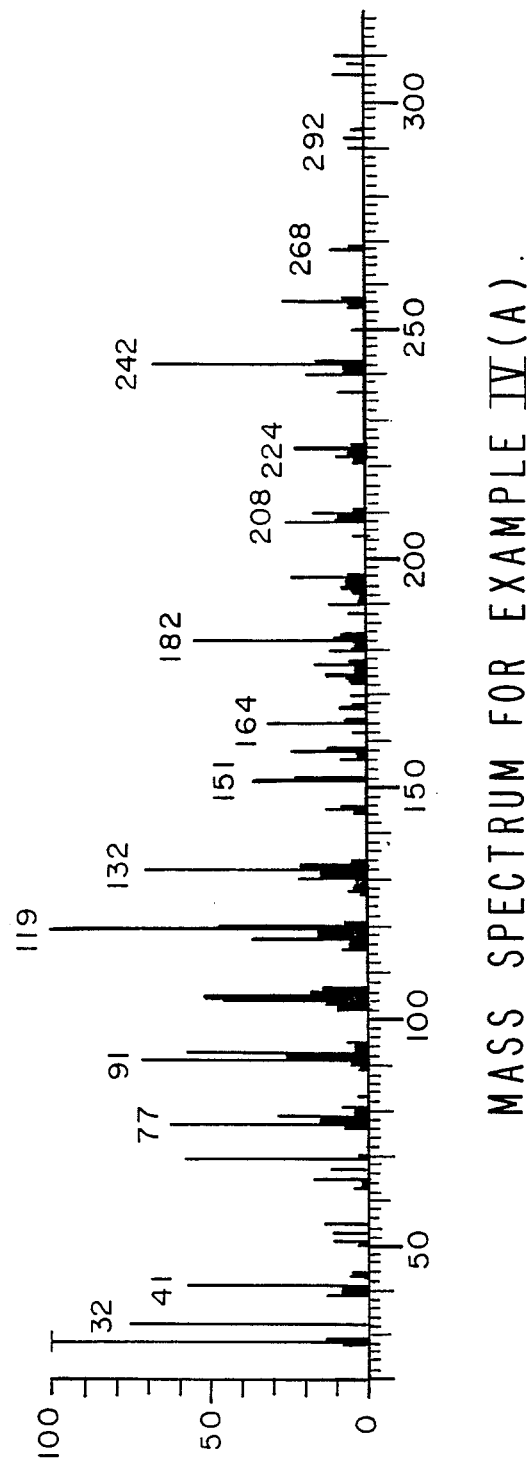

FIG. 14 is the mass spectrum for one of the compounds having the structures:

prepared according to Example IV(A).

Figure 16:
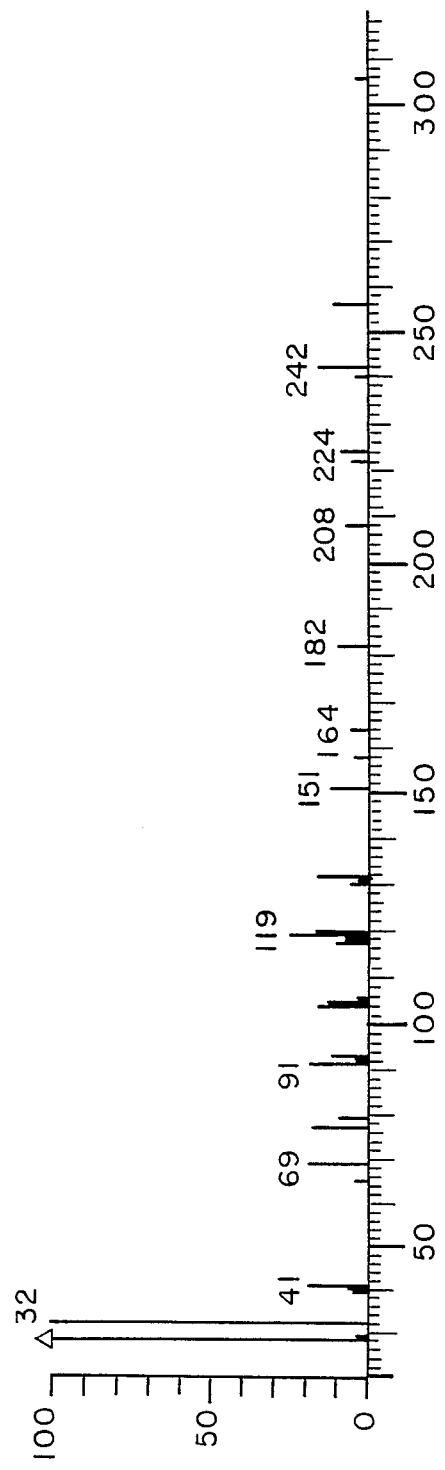

FIG. 16 is the mass spectrum for one of the compounds having one of the structures:

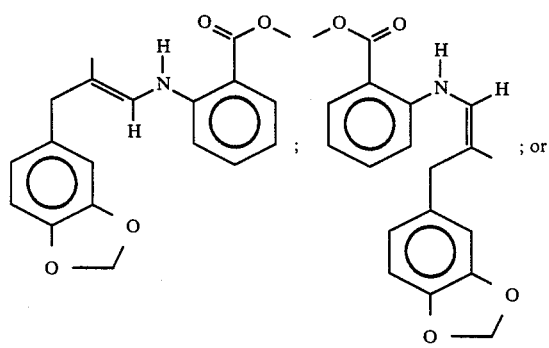

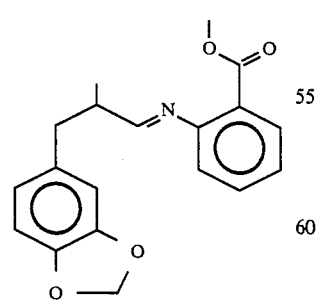

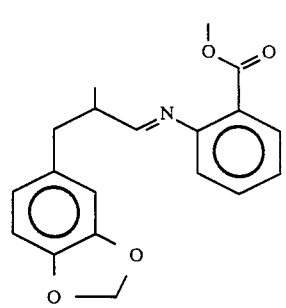

prepared according to Example IV(A).

Figure 15:
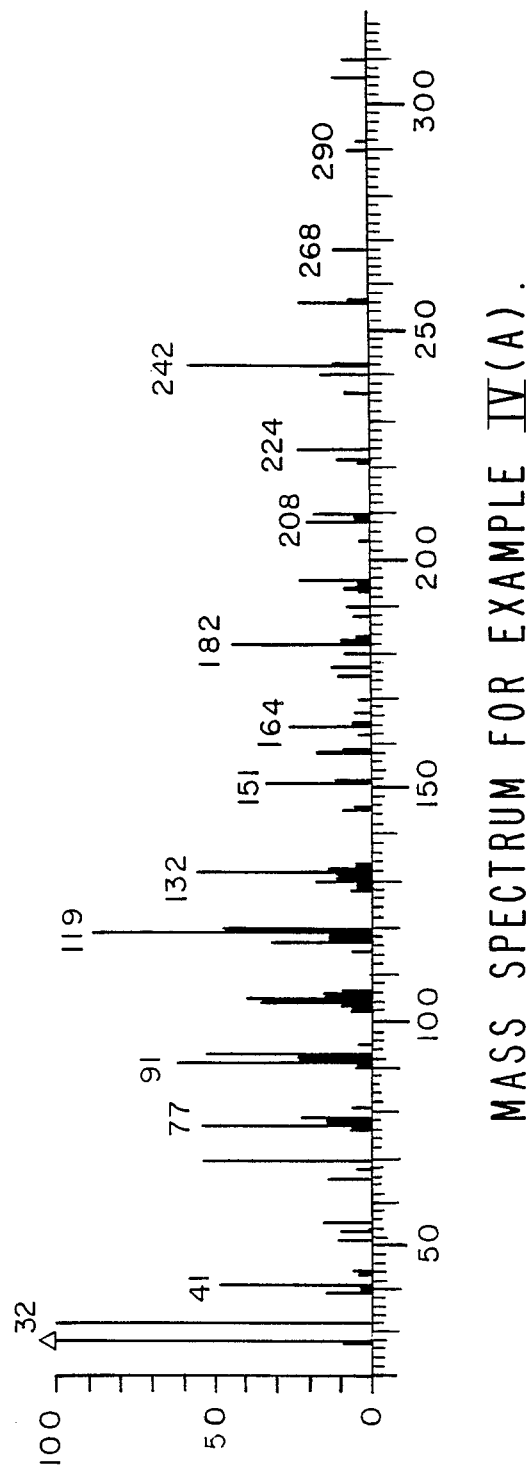

FIG. 15 is the mass spectrum for one of the compounds having one of the structures:

prepared according to Example IV(A).

Figure 17:
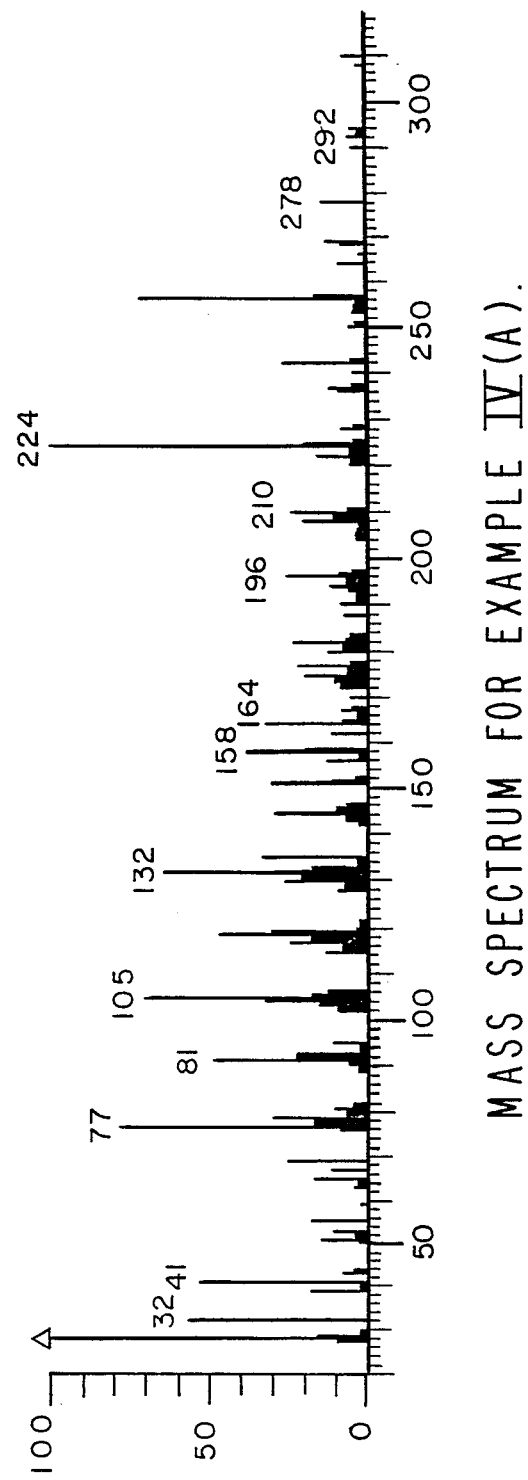

FIG. 17 is the mass spectrum for one of the compounds having one of the structures:

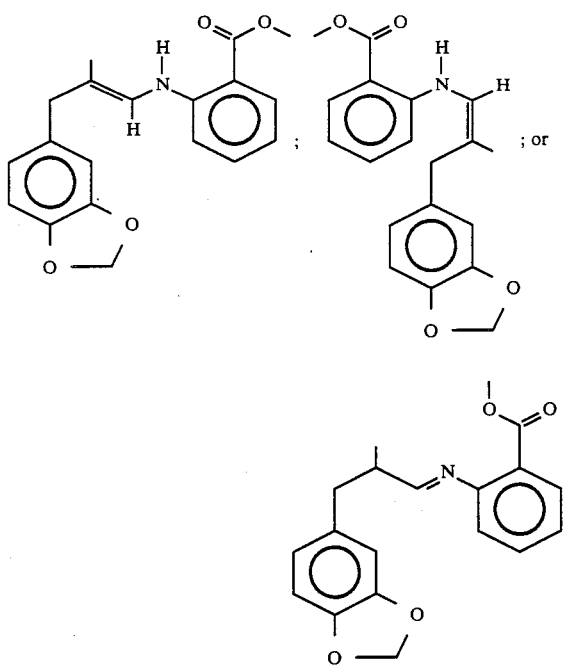

prepared according to Example IV(A).

Figure 18:
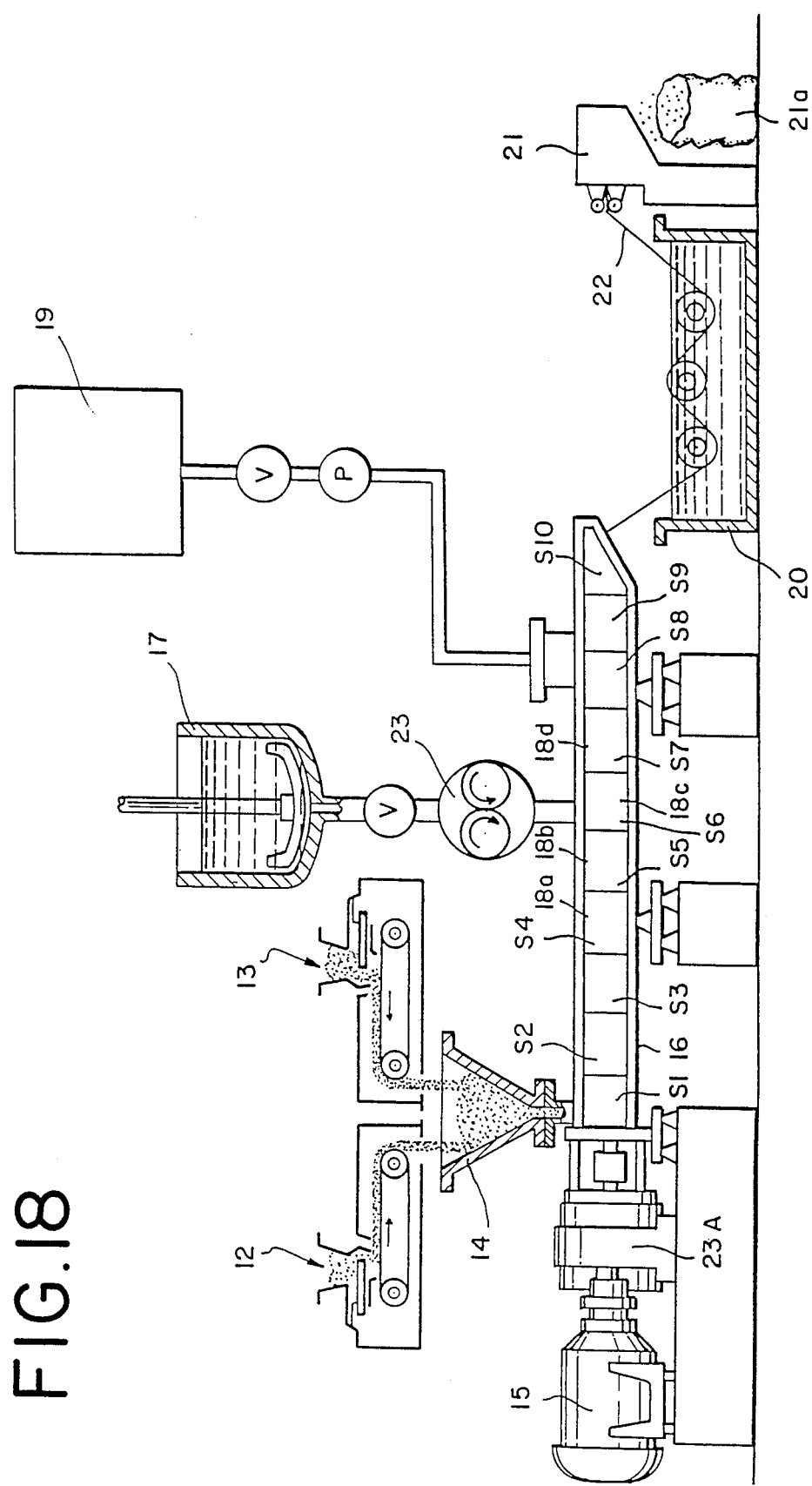

FIG. 18 is a cut-away side elevation schematic diagram of a screw extruder during the compounding of a resin with one of the schiff base compositions of our invention while simultaneously adding foaming agent into the hollow portion of the barrel of the extruder and incorporates pelletizing apparatus used in pelletizing the extruded foamed tow produced as a result of the extrusion operation.

Figures 19, 20:
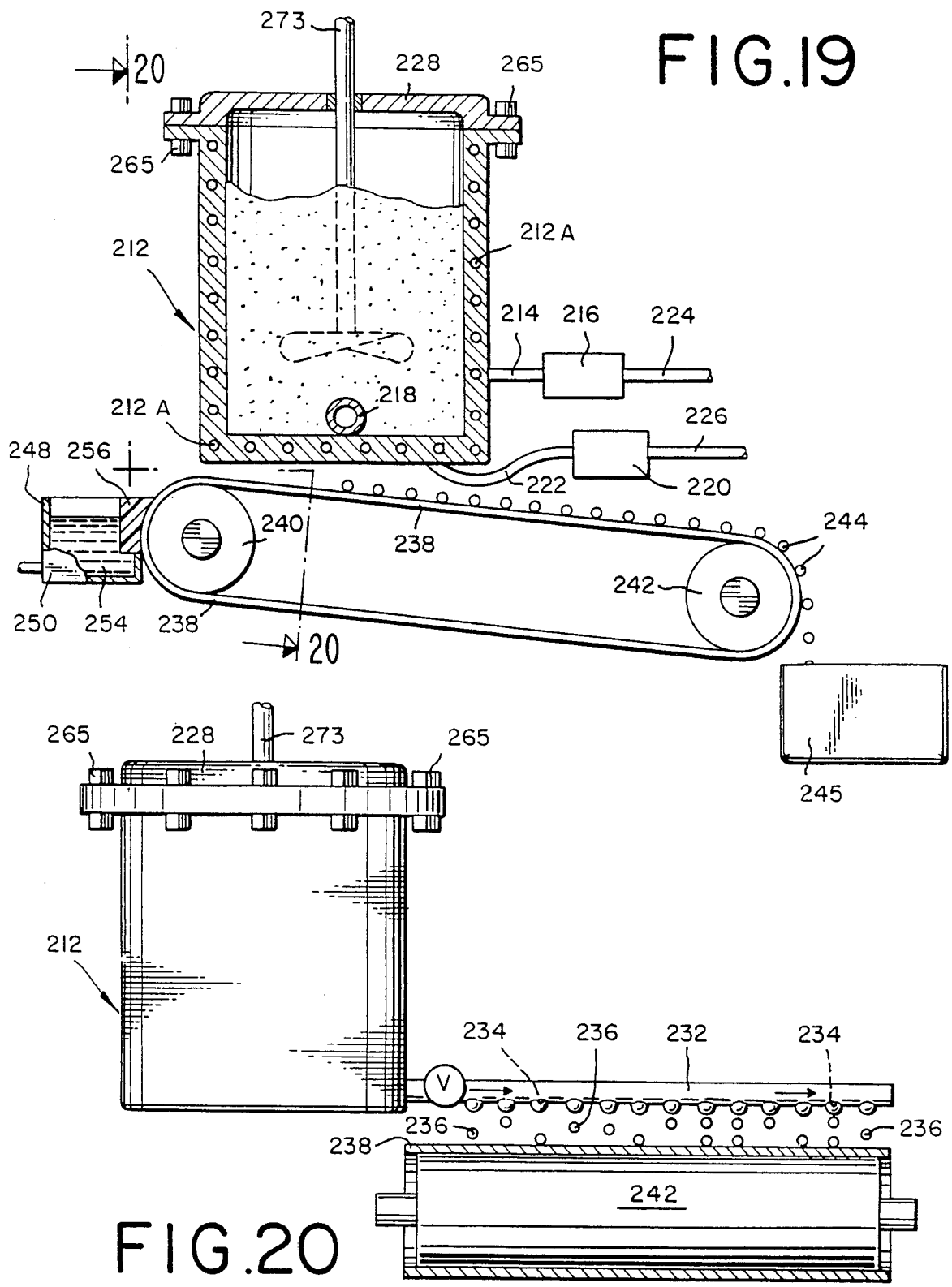

FIG. 19 represents a cut-away side elevation view of apparatus used in forming perfumed polymers which contain imbedded therein at least one of the schiff base compositions of matter of our invention.

FIG. 20 is a front view of the apparatus of FIG. 19 looking in the direction of the arrows.

DETAILED DESCRIPTION OF THE DRAWINGS

Referring to FIG. 18, FIG. 18 is a schematic cut-away elevation diagram of the extrusion and pelletizing apparatus useful in carrying out a process for incorporation of the schiff base compositions of our invention into polymers during the operation of said apparatus. Motor 15 drives the extruder screws located at 23A in barrel 16, the extruder being operated at temperatures in the range of about 150° up to about 250° C. At the beginning of the barrel resin at source 12 together with additives, e.g., opacifiers, processing aids, colors, pearlescent agents and densifiers at location 13 is added via addition funnel 14 into the extruder. Simultaneously (when the operation reaches "steady state", one or more of the schiff base compositions of our invention is added to the extruder at one, two or more of barrel segments 3–8 of the extruder (which may be a twin screw or single screw extruder) at locations 18a, 18b, 18c and 18d by means of gear pump 23 from source 17. From source 19 into barrel segments 5–10, the gaseous or liquid blowing agents, e.g., nitrogen, carbon dioxide and the like are added simultaneously with the addition of the schiff base compositions of our invention. The feed rate range of the resin is about 80–300 pounds per hour. The feed rate range of the schiff base compositions taken alone or further together with other perfumant is between 1 and 45% of the feed rate range of the resin. The blowing agent rate range is such that the pressure of the gas or the pressure over the liquid being fed into the extruder is between about 50 and 200 psig. If desired, the extruded ribbon or cylinder may be passed through water bath 20 and pelletizer 21 into collection apparatus 21a.

Referring to FIGS. 19 and 20, there is provided a process for forming scented polymer pellets (wherein the polymer may be a thermoplastic polymer such as low density polyethylene or polypropylene or a copolymer of ethylene and vinyl acetate or mixtures of polymers and copolymers such as copolymers of ethylene and vinyl acetate and polyethylene) such as pellets useful in the formation of plastic particles useful in fabricating cetain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 20 and 21, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymer and the perfuming substance which is at least one of the schiff base compositions of our invention or mixtures of schiff base compositions and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the schiff base compositions of our invention is quickly added to the melt. Generally, about 10–45 percent by weight of the resulting mixture of the perfumery substance is added to the polymer.

After the perfume material containing the schiff base compositions of our invention is added to the container 212 the mixture is stirred for a few minutes, for example, 5–15 minutes and maintained within the temperature ranges indicated previously by the heating coil 212A.

The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the schiff base compositions of our invention or mixture of perfume substance and one or more of the shiff base compositions of our invention, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is all or which contains one or more of the schiff base compositions of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

Our invention provides schiff base compositions and compositions of matter produced by means of the reaction of alkyl anthranilates having the structure:

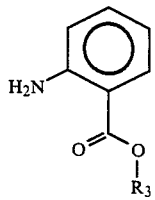

wherein $R_3$ is methyl or ethyl, for example, methyl anthranilate having the structure:

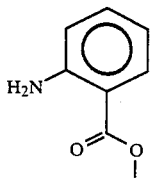

with aldehydes having the structure:

and helional having the structure:

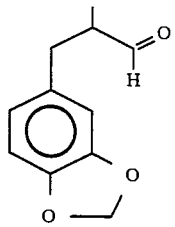

wherein the compound having the structure:

may be pinoacetaldehyde having the structure:

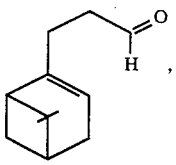

pinoisobutyraldehyde having the structure:

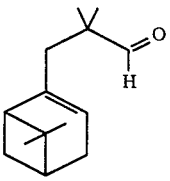

or lyral which is a mixture of compounds having the structures:

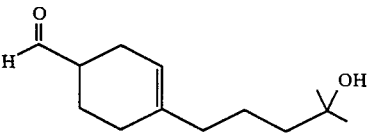

and

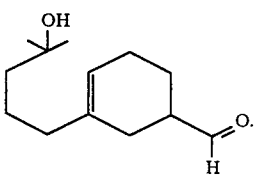

Our invention also relates to the deodorizing use of the reaction product of helional having the structure:

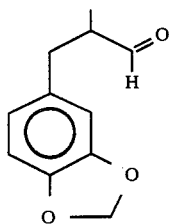

and alkyl anthranilates defined according to the structure:

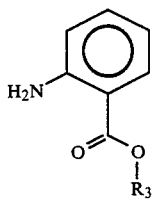

wherein $R_3$ is methyl or ethyl.

The reaction products of helional having the structure:

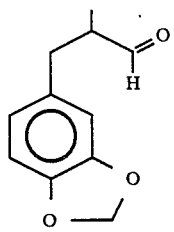

with the alkyl anthranilates have the structures:

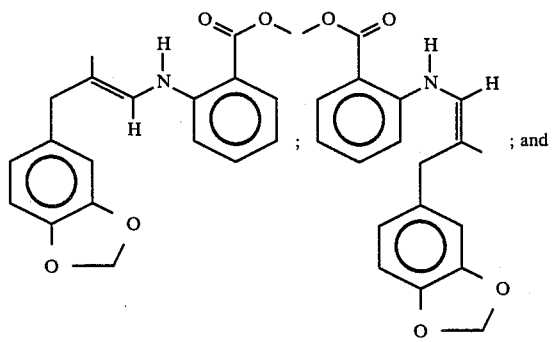

When the aldehydes of the structure:

(wherein R is defined, supra) are reacted with methyl anthranilate and helional, compounds having the structures:

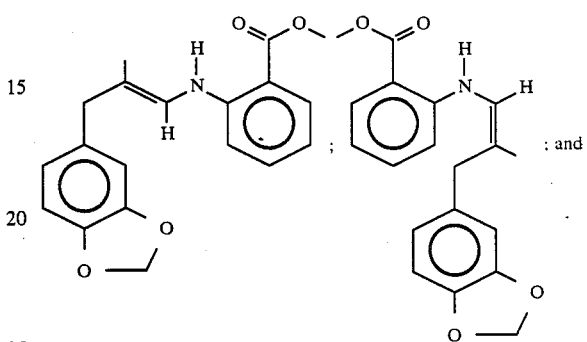

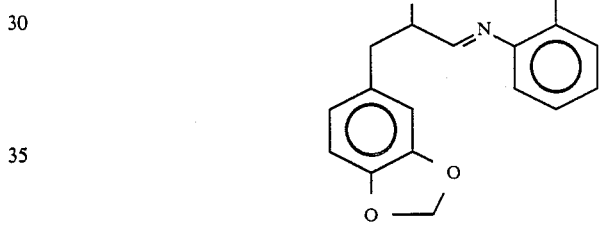

are produced along with one of the following groups of compounds:

(Group A): The mixture of compounds having the structures:

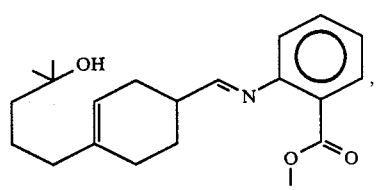

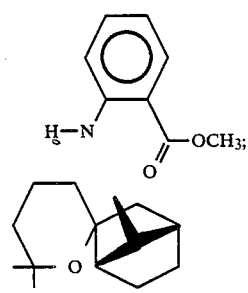

and

-continued

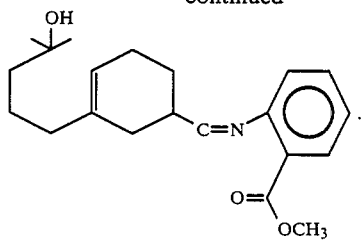

(Group B): The compounds having the structures:

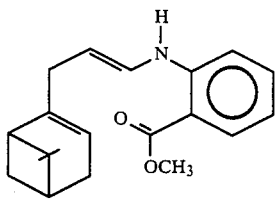

and

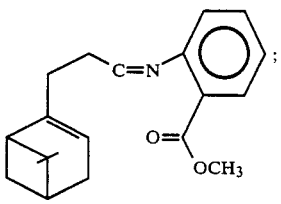

(Group C): The compound having the structure:

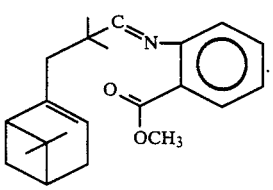

The reaction products of our invention are collectively termed "schiff base compositions"; but not all of the products produced according to the "schiff base" reaction set forth, supra, and specifically set forth, infra, contain the moiety:

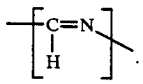

Thus, as will be seen, infra, the reaction of "helional" structure:

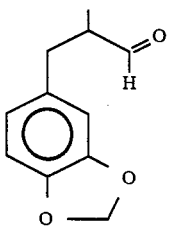

with the compound having the structure:

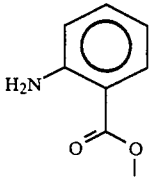

yields three compounds having the structures:

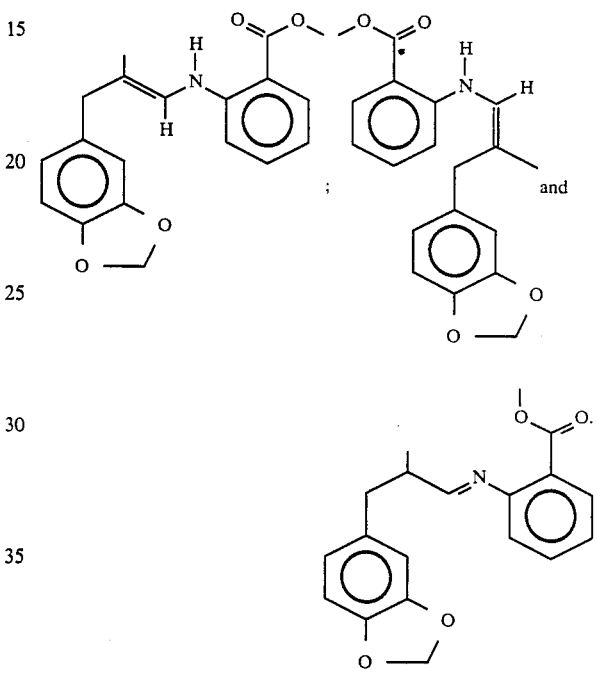

The resulting schiff base compositions of our invention produced according to the process of our invention are capable of augmenting or enhancing floral, oriental, citrus, lemony, melony, watermelon, green and concord grape aromas with watermelon, floral, oriental, citrus, lemony, melony, green, raspberry and concord grape tastes of foodstuffs, chewing gums, toothpastes, medicinal products and chewing tobaccos.

The schiff base compositions of our invention produced according to the process of our invention are also capable of modifying or enhancing the aroma characteristics of perfurme compositions, colognes and perfumed articles (including soaps, anionic, cationic, nonionic or zwitterionic detergents, fabric softener compositions, optical brightener compositions and drier-added fabric softener articles) and perfumed polymers by imparting thereto intense and substantive green, orange flower, fruity, ozoney, sweet anisic, melon, herbaceous, balsamic, walnut and floral aromas with grape, fruity, green, floral, anisic, ozoney, piney, melony and lemony topnotes, thus fulfilling a number of needs in the fields of perfumery and detergent and cosmetics manufacture.

The schiff base compositions of our invention are also capable of deodorizing detergent powders suitable for use in the washing of fabrics as well as detergent powders as well as hand soaps. Such detergent powders include bleaching compositions, for example, bleaching compositions comprising a peroxy bleach compound.

The schiff base compositions of our invention have deodorancy as measured by having a Lipoxidase-inhibiting capacity of at least 50% and a Raoult Variance ratio of at least 1.1 and a malodour reduction value of between about 0.25 up to 3.0 as measured by the malodour reduction value test disclosed in U.S. Pat. No. 4,663,068 the specification for which is incorporated by reference herein; and in addition, a deodorant value of from 0.50 up to 3.5 as measured by the deodorant value test disclosed in U.S. Pat. No. 4,304,679 the specification for which is incorporated by reference herein.

The reaction conditions to form the schiff base composition between the helional having the structure:

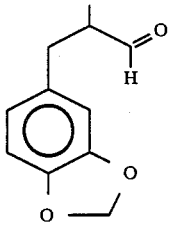

and/or aldehyde having the structure:

(wherein R is defined, supra) and the alkyl anthranilate having the structure:

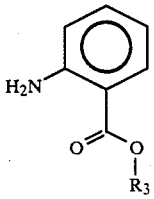

wherein $R_3$ is methyl or ethyl are as follows:

(i) the temperature of the reaction is in the range of from about 90° C. up to about 150° C.;

(ii) the pressure over the reaction mass may vary from about 3 mm/Hg. (vacuum) up to about 1 atmosphere with a preferable pressure of between about 5 and about 100 mm/Hg. pressure when no additional solvent is used and with a preferable pressure of about 1 atmosphere (reflux conditions) when a solvent inert to the reaction mass is used whereby water of reaction is azeotrope from the reaction mass during the course of the reaction;

(iii) the time of reaction may vary from about 5 up to about 15 hours with a preferred time of reaction of between about 6 and about 12 hours;

(iv) the mole ratio of helional having the structure:

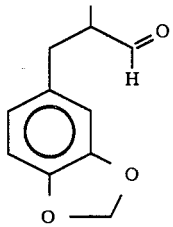

and/or aldehyde having the structure:

to alkyl anthranilate having the structure:

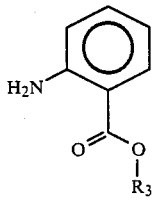

may vary from about 1:1 up to about 1.25:1 of total aldehyde:alkyl anthranilate with a preferred mole ratio of between about 1:1 and about 1.1:1 aldehyde:alkyl anthranilate; and (v) the reaction mass may be solvent free or a solvent may be used (e.g., toluene) which is inert to the reactants and reaction products and which is useful to cause azeotropic distillation of water of reaction from the reaction mass. However, a solvent free reaction mass is preferred.

At the end of the reaction, the reaction mass may be separated into its individual components and the reaction product may be purified as by fractional distillation of the schiff base composition or schiff base reaction product. From a practical standpoint, when a reaction mixture is created which gives rise to preferred perfumery properties or preferred deodorization properties or preferred flavor properties subsequent fractional distillation to the point of yielding an odor acceptable product and/or a flavor acceptable product and/or a deodorizing acceptable product is what is desired.

The following Table I sets forth reactants, schiff base reaction product structures (to the extent known) and organoleptic properties (from both a flavor and fragrance standpoint) of the resulting products.

TABLE I

| Reactants | Schiff Base Reaction Product Structures (to the extent known) | Perfumery and Flavor Properties |
|---|---|---|
| Helional having the structure: | Product produced according to Example | Perfumery Properties |

TABLE I-continued

| Reactants | Schiff Base Reaction Product Structures (to the extent known) | Perfumery and Flavor Properties |
|---|---|---|
| 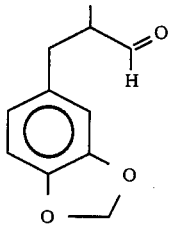 and methyl anthranilate having the structure: 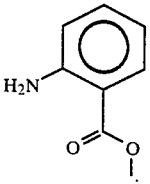 | I containing the compounds having the structures: 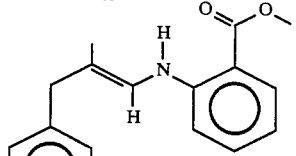 and 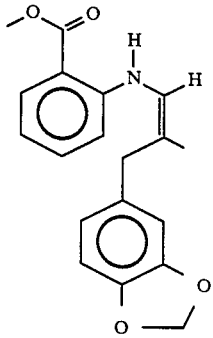 | A green orange flower, fruity, ozoney, sweet and anisic aroma with grape, fruity, green, floral, anisic and ozoney topnotes. |
| Pinoisobutylraldehyde:helional: methyl anthranilate in a mole ratio of 1:1:2 with pinoisobutylraldehyde having the structure: 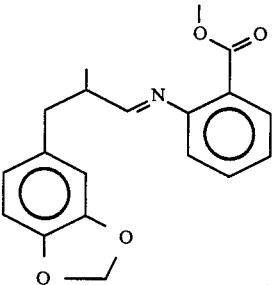 | Product produced according to Example III(A) containing the compounds having the structures: 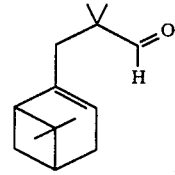 | Perfumery Properties A walnut, green, melony, ozoney aroma with floral, woody, animalic, walnut, green and ozoney topnotes. Flavor Properties |

TABLE I-continued

| Reactants | Schiff Base Reaction Product Structures (to the extent known) | Perfumery and Flavor Properties |
|---|---|---|
| | 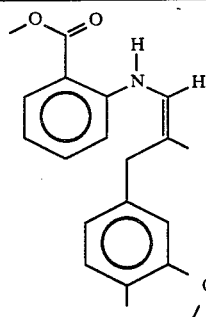 | A floral, oriental aroma with watermelon, floral and oriental taste nuances at 1 ppm. |
| | 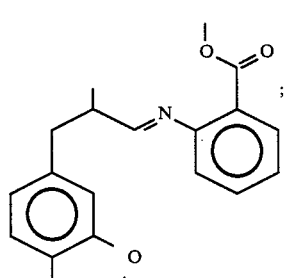 and 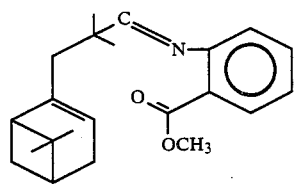 | |
| Pino isobutyraldehyde: helional:methyl anthranilate in a mole ratio of 1:2:3. | Product produced according to Example III(B) containing the compounds having the structures: 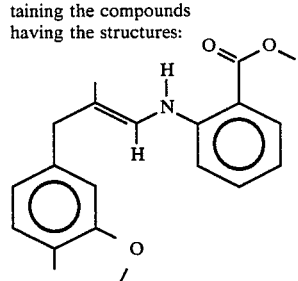 | Perfumery Properties<br><br>A green, floral, anisic, ozoney and fruity aroma with green, melon, ozoney, floral, anisic and animalic topnotes. |
| | 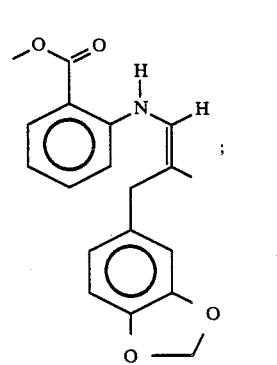 | Flavor Properties<br><br>A lemony and oriental aroma and taste profile at 1 ppm. |

TABLE I-continued

| Reactants | Schiff Base Reaction Product Structures (to the extent known) | Perfumery and Flavor Properties |
|---|---|---|
| Pino acetaldehyde: helional:methyl anthranilate in a mole ratio of 1:2:3, the pino acetaldehyde having the structure: 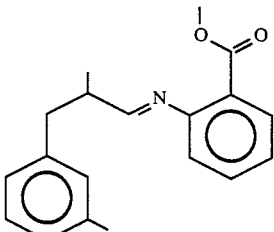 | 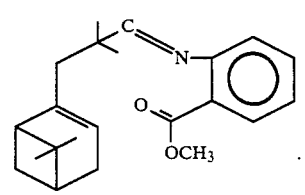 and 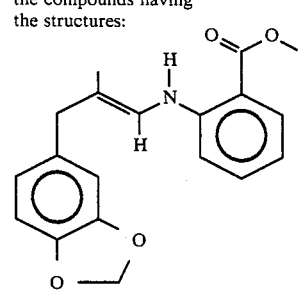 Product produced according to Example II containing the compounds having the structures: 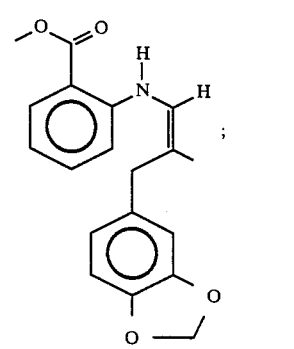 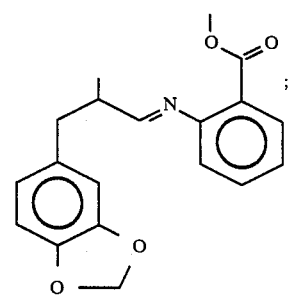 | Perfumery Properties A melony, herbaceous, sweet and balsamic aroma with piney, fruity and ozoney topnotes. Flavor Properties A melony, citrus, watermelon, green aroma with melony, citrus, green and raspberry taste nuances at 0.1 ppm. |

TABLE I-continued

| Reactants | Schiff Base Reaction Product Structures (to the extent known) | Perfumery and Flavor Properties |
|---|---|---|
| | 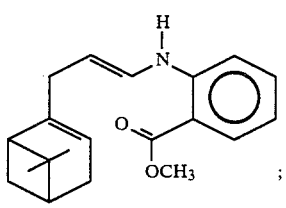 and 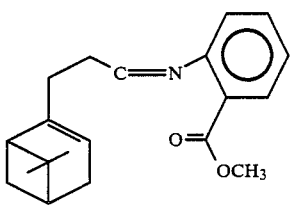 | |
| Helional:lyral:methyl anthranilate in a mole ratio of 1:2:3 with lyral being a mixture of compounds having the structures: 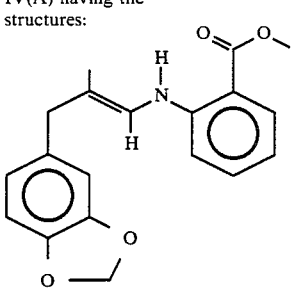 and 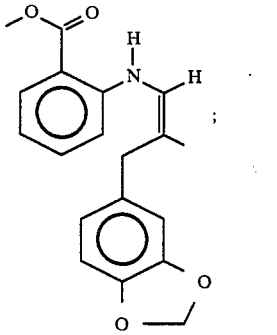 | Product produced according to Example IV(A) having the structures: 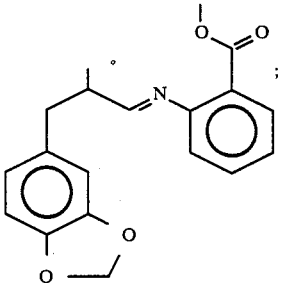 | Perfumery Properties A green, floral, ozoney aroma with green, floral, ozoney and lemony topnotes. Flavor Properties A floral and concord grape aroma and taste profile at 1 ppm. |

TABLE I-continued
| Reactants | Schiff Base Reaction Product Structures (to the extent known) | Perfumery and Flavor Properties |
|---|---|---|
| | 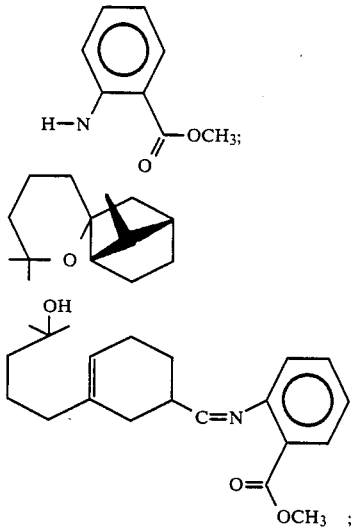 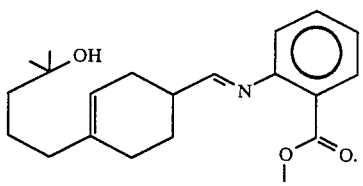 and | |
| Helional:lyral:methyl anthranilate in a mole ratio of 1:2:3. | Product produced according to Example IV(B) containing the compounds having the structures: 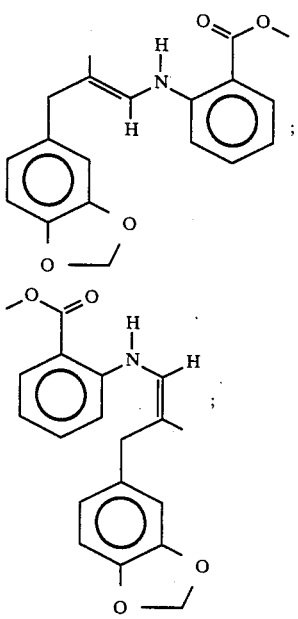 | Perfumery Properties A green, floral, and ozoney aroma with green and floral topnotes. |

TABLE I-continued

| Reactants | Schiff Base Reaction Product Structures (to the extent known) | Perfumery and Flavor Properties |
|---|---|---|

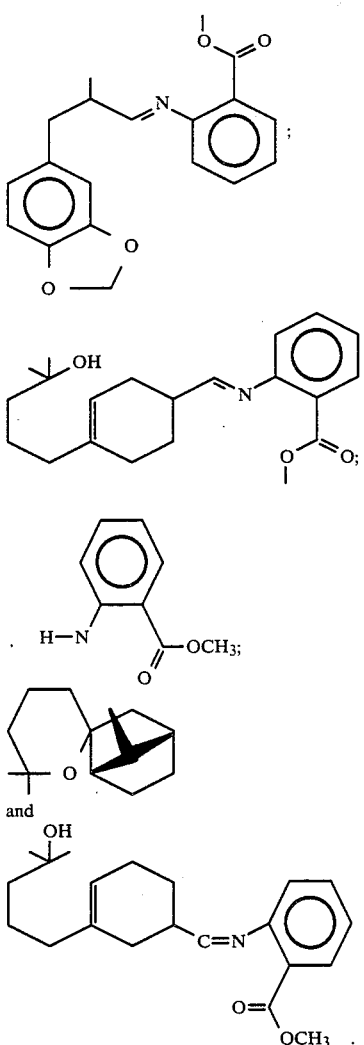

When one or more of the schiff base compositions of our invention is used as a food flavor adjuvant, the nature of the co-ingredients included with said schiff bases in formulating the product composition will also serve to alter the organoleptic characteristics of the ultimate foodstuffs treated therewith. As used herein in regard to flavors the term "alter" in its various forms means "supplying or imparting flavor character or notes to otherwise bland relatively tasteless substance or augmenting the existing flavor characteristic where a natural flavor is deficient in some regard or supplementing the existing flavor impression to modify its quality, character or taste".

As used herein, the term "foodstuff" includes both solid and liquid ingestible materials which usually do but need not have nutritional value. Thus, foodstuffs include soups, convenience foods, beverages, dairy products, candies, fruit cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. Accordingly, such materials which may in general be characterized as flavoring adjuvants or vehicles comprise broadly stabilizers, thickeners, surface active agents, conditoners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3-tertiary butyl-4-hydroxyanisole), butylated hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agaragar; carrageenan; cellulose and cellulose derivatives such as carboxymethyl cellulose and methyl cellulose; natural and synthetic gums such as gum arabic, gum tragacanth; gelatin; proteinaceous materials; lipids, carbohydrates; starches, pectins, and emulisifiers, e.g., mono- and diglycerides of fatty acids, skim milkl powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, turmeric and curcumin and the like; firming agents such as aluminum sodium sulfate, calcium chloride and calcium gluconate; texturizers; anti-caking agents, e.g., aluminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, butyric acid, caproic acid, caprylic acid, formic acid, 2-hexenoic acid, 3-hexenoic acid, isobutyric acid, isovaleric acid, propionic acid and valeric acid; ketones and aldehydes, e.g., acetaldehyde, acetone, acetyl methyl carbinol, acrolein, diacetyl, $\beta,\beta$-dimethylacrolein, hexanal, 2-hexenal, cis-3-hexenal, 4(p-hydroxyphenyl)-2-butanone, alpha-ionone, $\beta$-ionone, and 2-pentenal; alcohols, such as 1-butanol, trans-2-buten-1-ol, ethanol, geraniol, 1-hexanol, cis-3-hexen-1-ol, 3-methyl-3-buten-1-ol, 1-pentanol, 1-penten-3-ol; esters, such as butyl acetate, ethyl acetate, ethyl butyrate, ethyl crotonate, ethyl propionate, 2-hexenyl acetate, 2-hexenyl butyrate, hexyl acetate, hexyl butyrate, isoamyl acetate, isopropyl butyrate, methyl butyrate, methyl caproate, methyl caprylate, propyl acetate, amyl acetate, amyl butyrate, benzyl salicylate, dimethyl anthranilate, ethyl methylphenylglycidate, ethyl succinate, isobutyl cinnamate, and terpenyl acetate; essential oils such as jasmine absolute, rose absolute, orris absolute, lemon essential oil and vanilla; lactones; sulfides, e.g., methyl sulfide and other materials such as maltol and citral as well as natural raspberry oil, orange oil, mango extract, pickled mango extract, natural cranberry juice, strawberry juice concentrate and grape juice concentrate.

The specific flavoring adjuvants selected for use may be either solid or liquid, depending upon the desired physical form of the ultimate product, i.e., foodstuff, whether simulated or natural, and should, in any event, be capable of providing an environment in which the schiff bases of our invention can be disbursed or admixed to provide a homogeneous medium. In addition, selection of one or more adjuvants, as well as the quantities thereof, will depend upon the precise organoleptic grape character desired in the finished product. Thus, in the case of flavoring compositions, ingredient selection will vary in accordance with the foodstuff to which the flavor and aroma are to be impaired. In contradistinction, in the preparation of solid products, e.g., simulated foodstuffs, ingredients capable of providing normally solid compositions should be selected such as various cellulose derivatives.

As will be appreciated by those skilled in the art, the amount in which the schiff base compositions of our invention employed in a particular instance can vary over a relatively wide range whereby its desired organoleptic effects (having reference to the nature of the product) are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for the purposes of enhancing the composition merely deficient in natural flavor or aroma. Thus, the primary requirements is that amount which is effective, i.e., sufficient to alter the organoleptic characteristics of the parent composition, whether foodstuff per se or flavoring composition. Thus, the use of insufficient quantities in which the schiff base compositions of our invention will, of course, substantially vitiate any possibility of obtaining the desired results while excess quantities prove needlessly costly and in extreme cases, may disrupt the flaovr-aroma balance, thus proving self-defeating. Accordingly, the terminology "effective amount" and "sufficient amount" is to be accorded a significance in the context of the present invention consistent with the obtention of desired flavoring effects.

Thus and with respect to ultimate food compositions, it has been found that quantities in which the schiff base compositions of our invention ranging from a small but effective amount, e.g., 0.02 parts per million up to about 50 parts per million by weight based on total composition are suitable. Concentrations in excess of the maximum quantity stated are not normally recommended since they fail to provide commensurate enhancement of organoleptic properties. In those cases wherein in which the schiff bases of our invention is added to the foodstuff as an integral component of the flavoring composition, it is, of course, essential that the total quantity of flavoring composition employed be sufficient to yield an effective schiff base concentration in the foodstuff product.

The composition described herein can be prepared according to conventional techniques well known as typified by cake batters and fruit juices and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing the schiff bases of our invention with, for example, gum arabic, gum tragacanth, carrageenan and the like and thereafter spray-drying the resultant mixture whereby to obtain the particulate solid product. Prepared flavor mixes in powder form, e.g., a raspberry flavored powder are obtained by mixing dried solid, components, e.g., starch, sugar and the like and the schiff bases of our invention in a dry blender until the requisite degree of uniformity is achieved.

It is presently preferred to combine the schiff base compositions of our invention with the following adjuvants:

Parahydroxybenzyl acetone;
Vanilin;
Maltol;
Alpha-Ionone;
Beta-Ionone;

Isobutyl acetate;
Ethyl butyrate;
Dimethyl sulfide;
Acetic acid;
Acetaldehyde;
4-(2,6,6-trimethyl-1,3-cyclohexadien-1-yl)-2-butanone;
4-(6,6-dimethyl-2-methylene-3-cyclohexen-1-yl)-2-butanone;
2-(4-hydroxy-4-methylpentyl)norbornadiene produced according to Example I of U.S. Pat. No. 3,911,028;
Beta-Damascone(1-crotonyl-2,6,6-trimethylcyclohex-1-ene)
Beta-Damascenone(1-crotonyl-2,6,6-trimethylcyclohexa-1,3-diene);
Beta-cyclohomocitral(2,6,6-trimethylcyclohex-1-ene carboxaldehyde);
Isoamyl butyrate;
Cis-3-hexenol-1;
Elemecine(4-allyl-1,2,6-trimethoxybenzene);
Isoelemecine(4-propenyl-1,2,6-trimethoxybenzene);
Ethyl ester of 2-hydroxy butyric acid;
Ethyl-2-methyl-3-pentenoate;
Ethyl ester of 3-hydroxy butyric acid;
Orange oil;
Lemon oil;
Grape juice concentrate;
Cranberry juice concentrate;
Mango extract; and
Pickled mango extract.

The schiff base compositions prepared in accordance with the process of our invention and one or more auxiliary perfume ingredients including, for example, alcohols other than any alcohols existing in the schiff base compositions of our invention, aldehydes, ketones, terpinic hydrocarbons, nitriles esters other than any existing in the schiff base compositions of our invention, lactones, natural essential oils and synthetic essential oils may be admixed so that the combined odors of the individual components produce a pleasant and desired fragrance, particularly, and preferably, in pine, floral, lavender and "fresh air" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the over-all sensory effect of the perfume composition will be at least the sum total of the effects of each of the ingredients. Thus, schiff base compositions prepared in accordance with the process of our invention can be used to alter, modify or enhance the aroma characteristics of a perfume composition, for example, by utilizing or moderating the olfactory reaction contributed by another ingredient in the composition.

The amount of schiff base composition prepared in accordance with the process of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.01% of schiff base compositions prepared in accordance with the process of our invention and less than 50% of schiff base derivatives prepared in accordance with the process of our invention or even less (e.g., 0.005%) can be used to impart green, orange flower, fruity, ozoney, sweet anisic, melony, herbaceous, balsamic, walnut and floral aromas with grape, fruity, green, floral, anisic, ozoney, piney, melony and lemony topnotes to solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

The schiff base compositions prepared in accordance with the process of our invention is useful (taken alone or together with other ingredients in perfume compositions) as (an) olfactory component(s) in detergents and soaps, space odorants and deodorants perfumes, colognes, toilet water, bath preparations, such as creams, deodorants, hand lotions and sun screens; powders, such as talcs, dusting powders, face powders, and perfumed polymers and articles of manufacture produce from said perfumed polymers. When used as (an) olfactory component(s) as little as 0.2% of schiff base compositions prepared in accordance with the process of our invention will suffice to impart an intense and substantive green, orange flower, fruity, ozoney, sweet anisic, melony, herbaceous, balsamic, walnut and floral aromas with grape, fruity, green, floral, anisic, ozoney, piney, melony and lemony topnotes to floral, piney, lemony, rose and "fresh air" formulations. Generally, no more than 6% of one or more schiff base compositions of our invention based on the ultimate end product is required in the perfumed article composition. Accordingly, the range of schiff base compositions in the perfumed articles is from about 0.2% by weight of the schiff bases up to about 6% by weight based on the perfumed article. In addition, the perfume composition or fragrance composition of our invention can contain a vehicle or carrier for one or more of the schiff base compositions prepared in accordance with the process of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g., gum arabic, guar gum or xanthan gum) or components for encapsulating the composition (such as gelatin) as by coacervation; or such as urea-formaldehyde polymer forming a capsule shell around a liquid perfumed center).

Our invention also relates to the utilization of controlled release technology for the controlled release of perfumes into gaseous environments from polymers such as mixtures of epsilon polycaprolactone polymers and polyethylene which polyepsilon caprolactone polymers are defined according to at least one of the structures:

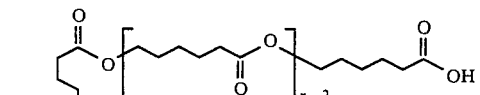

and/or

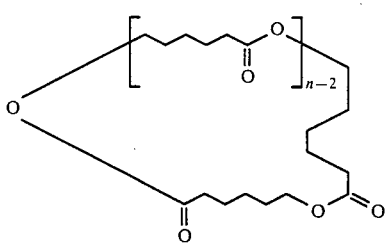

wherein "n" is from about 50 up to about 1,200 with the proviso that the average "n" in the system varies from about 150 up to about 700 according to the mathematical statement:

[700 ≧ n ≧ 150]

with the term "n" being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$dM_1/dl = k_1 e^{-k_2 t}$$

wherein $k_1$ and $k_2$ are constants. According to Kydonieus, "Controlled Release Technologies: Methods, Theory, and Applications" (cited, supra, the amount of perfume composition released is proportional to time as long as the concentration of perfume material present, e.g., the schiff base compositions of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release constant (zero order) as long as the surface area does not change during the erosion period. This is the case with the polymers containing the schiff base compositions of our invention.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE TERMOPLASTIC POLYMERS PCL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such as hydroquinone or compounds having the formula:

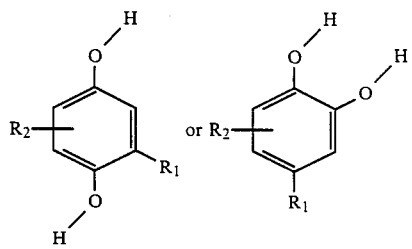

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfer with the functional fluids dissolved and/or adsorbed into the polymeric matrix.

The method of incorporating the schiff base compositions of our invention or perfume compositions containing same into the polymers may be according to the technique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylene-polyepsilon caprolactone polymer mixture (50:50) is mixed with one of the schiff base compositions of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700: polyethylene in molten form is admixed with a high percentage of one of the schiff base compositions of our invention and the mixture is solidified in the form of pellets or beads. These pellets or beads thus contain a high percentage of schiff bases (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference hererin.

In accordance with the present invention at least one of the schiff base compositions of our invention is added to the polymer in a large closed container or drum which is maintained under controlled temperature conditions while the polymer in a melted condition is mixed with at least one of the schiff bases under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one of the schiff base compositions of our invention is permitted to drip through the orifices onto a continuously moving, cooled conveyor upon which the polymer containing at least one of the schiff base compositions of our invention solidifies into small size pellets with the perfume imprisoned therein. The apparatus useful in conjunction with this process advantageously includes a conveyor of a material which will not adhere to the polymer which contains at least one of the schiff base compositions of our invention.

In order that the droplets form into uniform pellets or beads, the conveyor is continuously washed with a liquid such as water to maintain the surface relatively cool. The pellets are delivered by the conveyor into a container and packaged for shipment.

The following Examples I–IV serve to illustrate processes for preparing the schiff base compositions of our invention. The examples following Example IV are illustrative of the organoleptic utilities of the schiff base compositions as well as te deodorizing utilities of the schiff base compositions of our invention and the deodorizing capabilities of the reaction product of helional and methyl anthranilate which is also part of our invention.

All parts and percentages given herein are by weight unless otherwise specified.

EXAMPLE I

Preparation of Schiff Base of Methyl Anthranilate and Helional

Reaction:

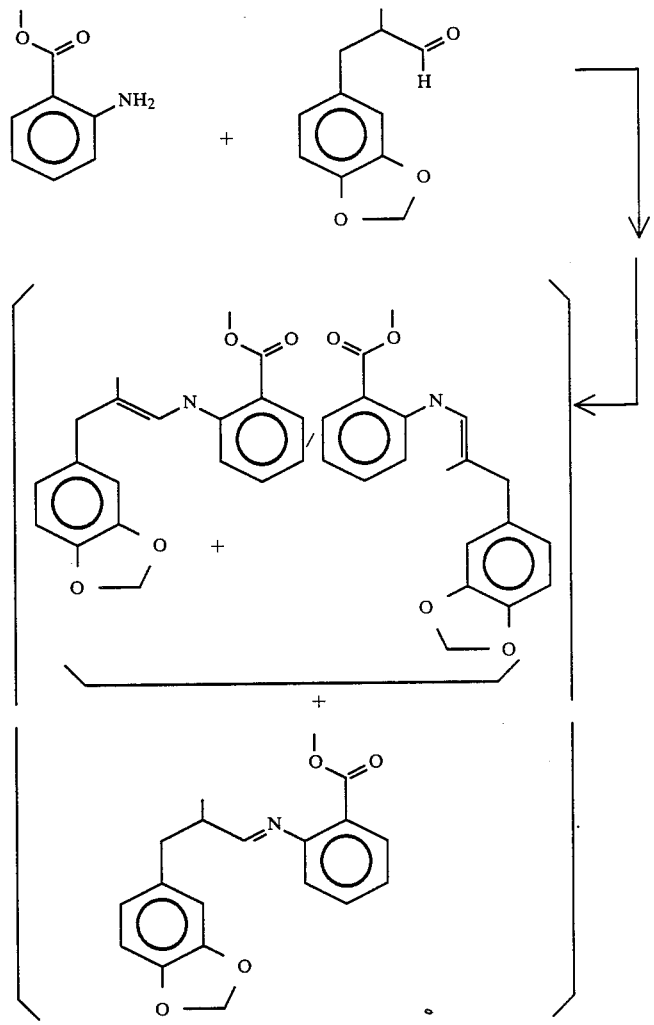

Into a 1 liter 3 neck reaction flask equipped with stirrer, thermometer, heating mantle and aziotropic take-off apparatus is placed 192.2 grams of helional (1.0 moles) having the structure:

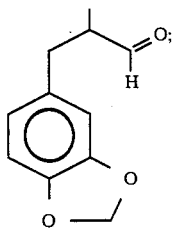

and 300 ml of dry toluene. The reaction mass is heated to reflux and 18 ml of water (1 mole) was aziotroped off over a period of 3 hours. By the same manner most of the remaining toluene is removed. A 100 grams of the crude reaction product is then molecular distilled up to a pot temperature of 200° C. Four fractions are obtained. NMR analysis indicates that the reaction mass contains the isomers having the structures:

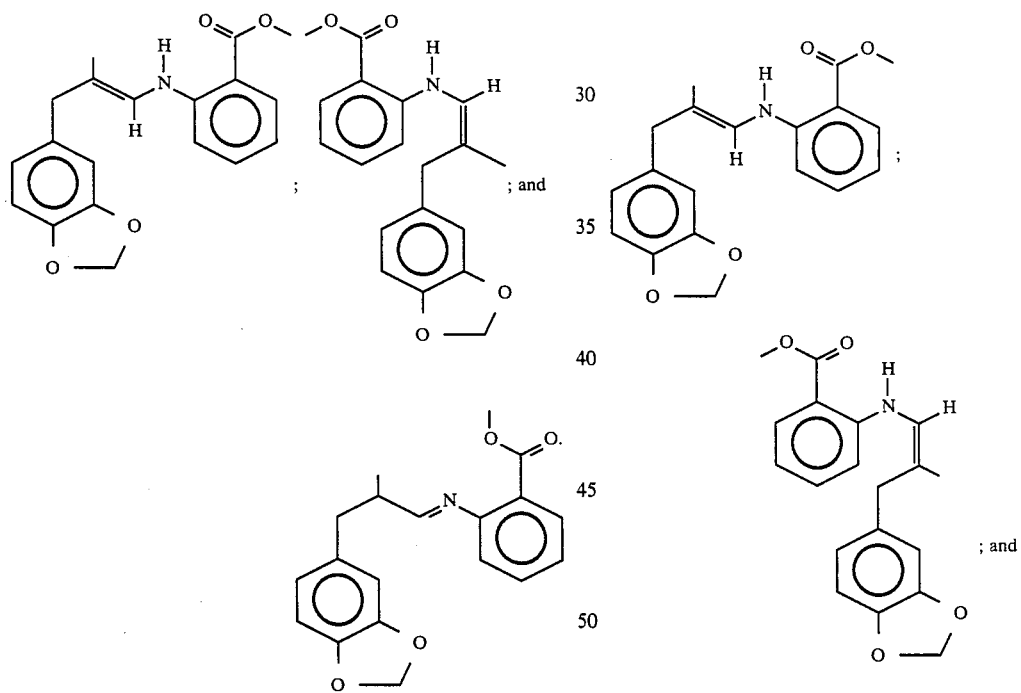

The resulting product has a green, orange flower, fruity, ozoney, sweet and anisic aroma with grape, fruity, green, floral, anisic and ozoney topnotes.

Figure 1:
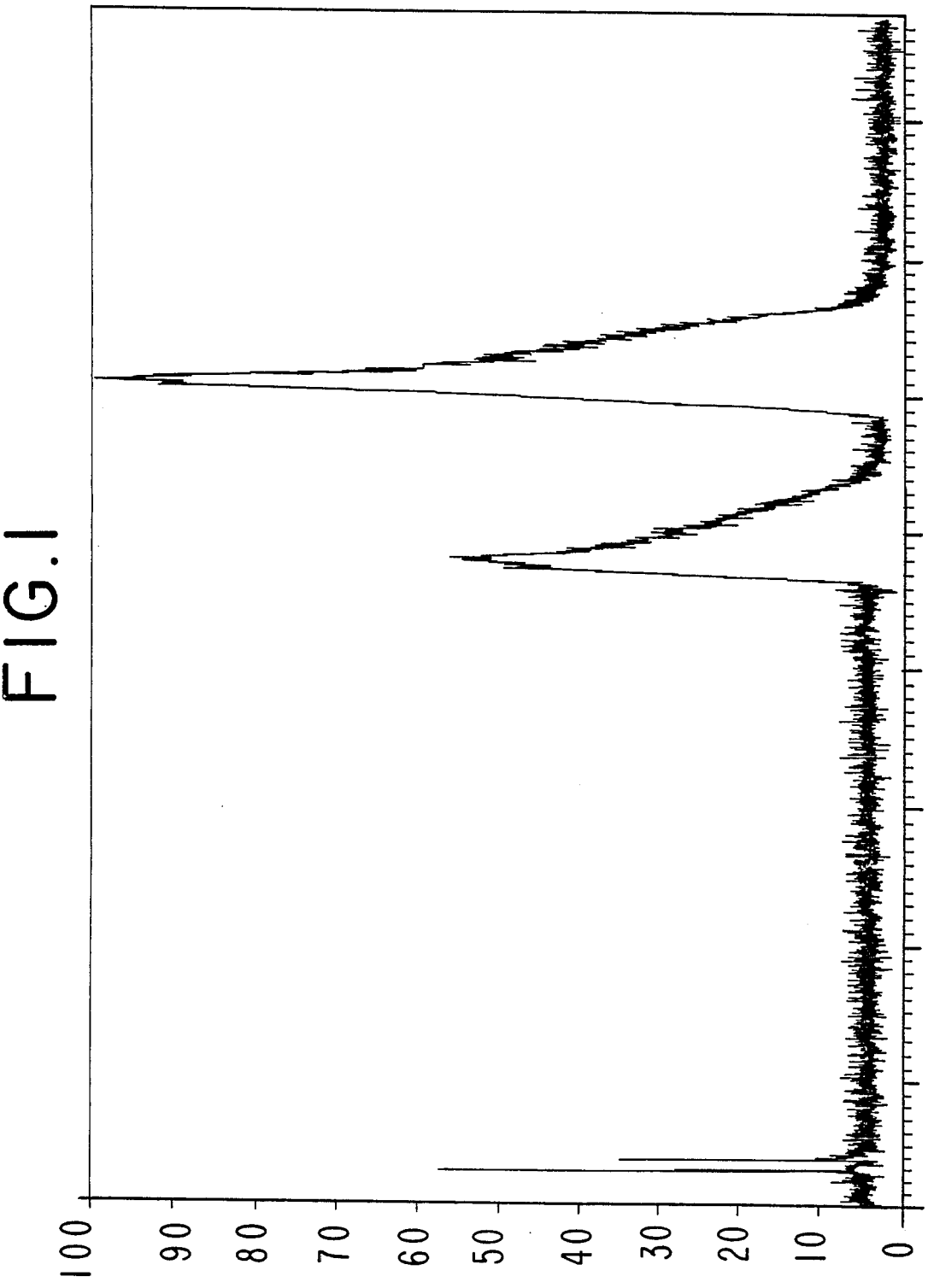
FIG. 1 is the GC spectral scan for the reaction product of Example I, the reaction product of methyl anthranilate having the structure.

FIG. 1 is the GC spectral scan for the resulting product (Conditions: 50 m×0.32 mm OV-1 fused silica column programmed at 225° C. isothermal).

FIG. 2 is the mass spectrum for one of the isomers of the resulting reaction product.

FIG. 3 is the NMR spectrum for the compound having the structure:

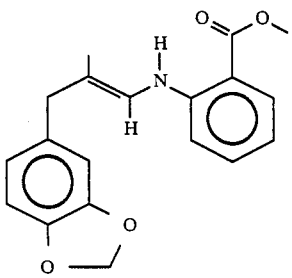

prepared according this example.

EXAMPLE I(A)

Preparation of Schiff Base of Methyl Anthranilate and Helional (Alternative Preparation)

Into a 500 ml reaction flask equipped with mechanical stirrer, thermometer and vacuum attachment is placed 75.5 grams of methyl anthranilate and 96.0 grams of helional. The reaction mass is heated at 90° C. with stirring for 3.5 hours at a vacuum of 30 mm/Hg.

NMR analysis and GLC analysis yield the information that the resulting structures are:

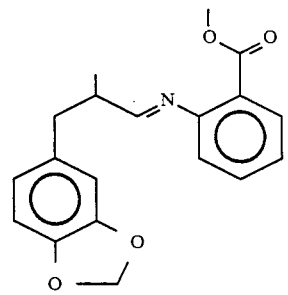

The resulting product has a green, orange flower, fruity, ozoney, sweet and anisic aroma with grape, fruity, green, floral, anisic and ozoney topnotes and is useful for its deodorizing properties as set forth in the following examples.

EXAMPLE II

Preparation of Schiff Base Reaction Product of Methyl Anthranilate, Pinoacetaldehyde and Helional Reaction:

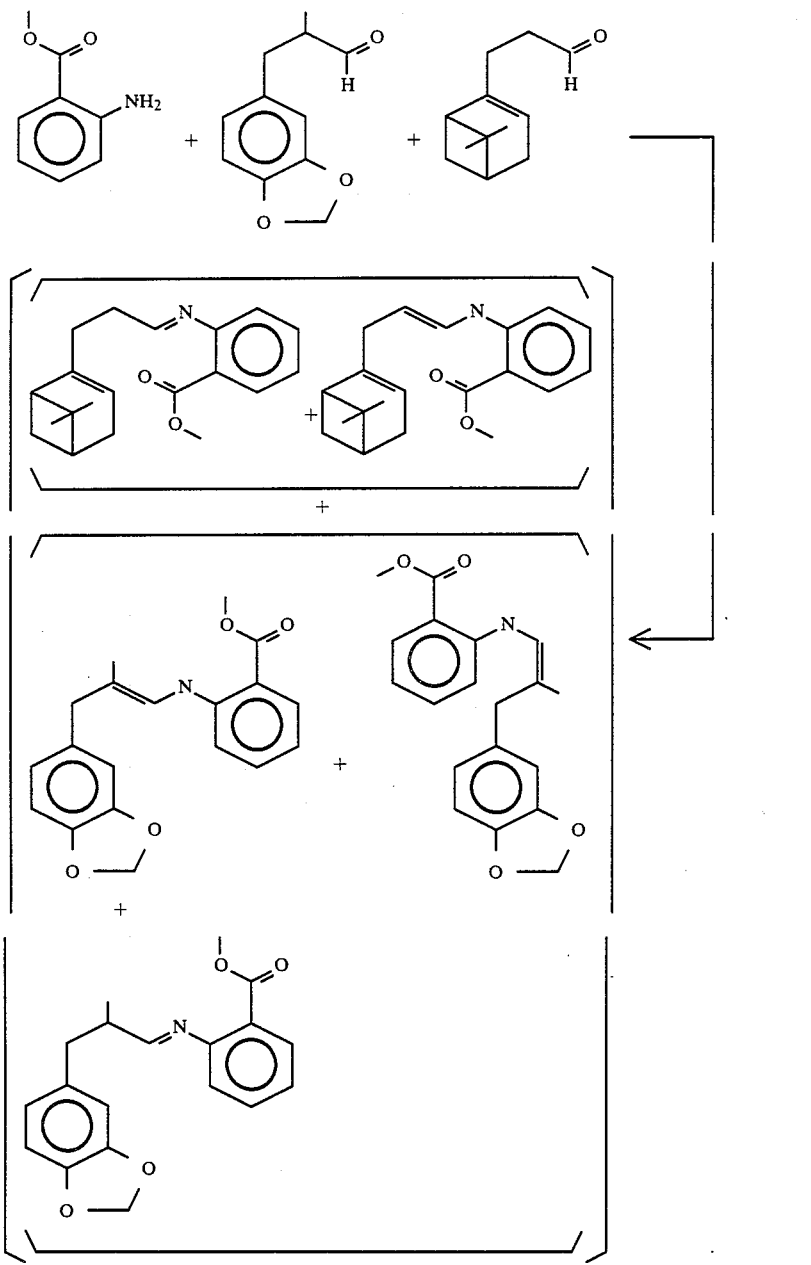

Into a 2 liter reaction flask equipped with thermometer, mechanical stirrer, addition funnel, vacuum apparatus and heating mantle are placed 377.5 grams (2.50 moles) of methyl anthranilate. The methyl anthranilate is heated to 50° C. and while maintaining the methyl anthranilate at 50° C., 153 grams of pino acetaldehyde and 288 grams of helional is added dropwise over a period of 15 minutes with stirring. After addition is complete the reaction mass is placed under 50 mm/Hg. vacuum and heated to 125° C. for a period of 7 hours.

At the end of the 7 hour period, the reaction mass is removed and frationally distilled yielding the following reaction products:

-continued

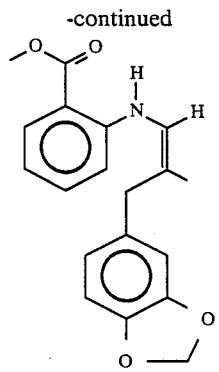

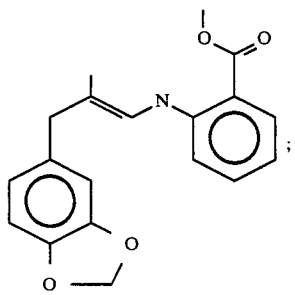
;

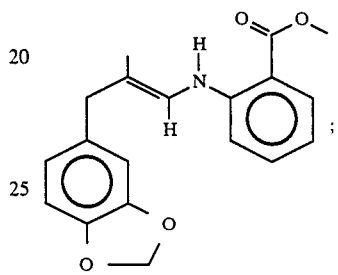
; and

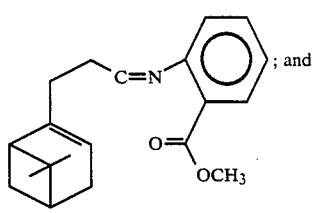
and

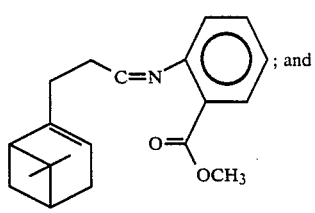

The resulting reaction product has from a fragrance standpoint a melony, herbaceous, sweet, balsamic aroma with piney, fruity and ozoney topnotes. From a flavor standpoint the resulting reaction product has a melony, citrus, watermelon, green aroma with a melony, citrus, watermelon, green and raspberry taste profile at 0.1 ppm.

FIG. 4 is the GC spectral scan for the resulting reaction product.

FIGS. 5 and 6 are mass spectra of the compounds (individually) having the structures:

-continued

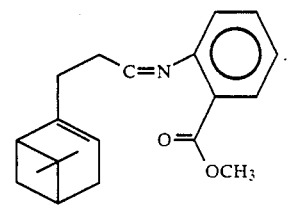

FIG. 7 is the mass spectrum for one of the compounds having one of the structures:

;

; or

EXAMPLE III(A)

Preparation of Schiff Base Reaction Product of Pinoisobutylraldehyde:Helional:Methyl Anthranilate with a Mole Ratio of Pinoisobutyraldehyde:Helional:Methyl Anthranilate Being 1:1:2

Reaction:

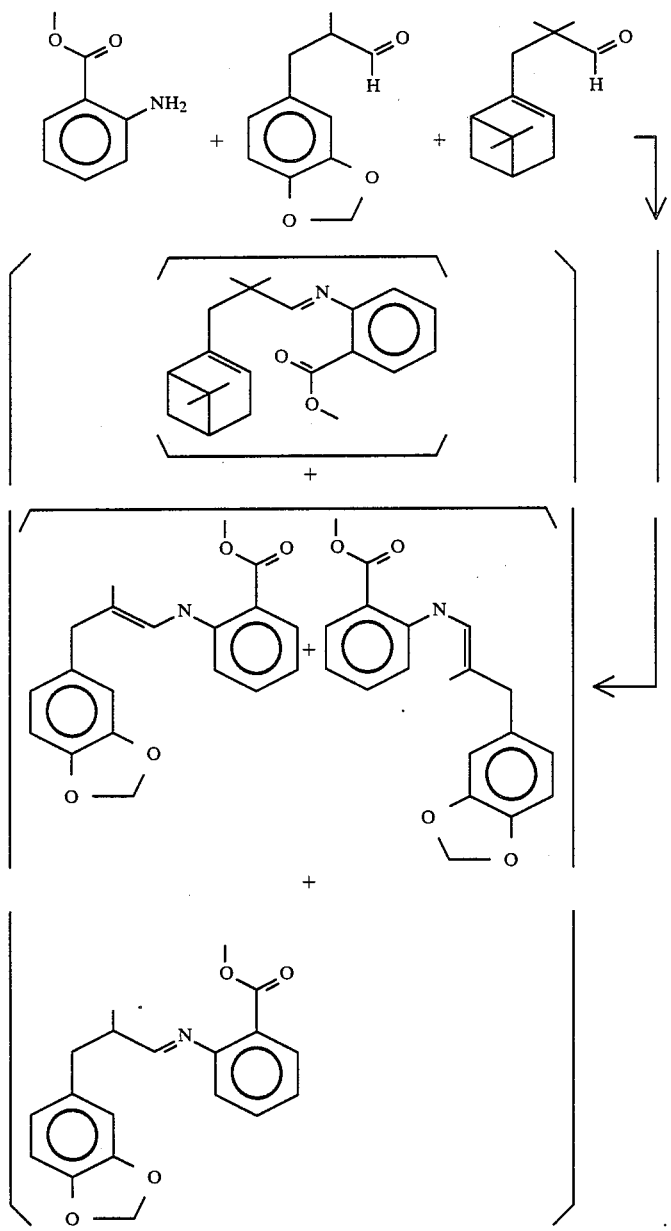

Into a 2 liter reaction flask equipped with stirrer, thermometer, heating mantle, vacuum apparatus and addition funnel is placed 2 moles of methyl anthranilate (302 grams). The methyl anthranilate is heated to 50° C. at atmospheric pressure. While maintaining the reaction mass at 50° C., one mole (142 grams) of helional and one mole (206 grams) of pino acetaldehyde are added to the reaction mass. When all the aldehyde is added the reaction mass is placed under 50 mm/Hg. vacuum and heated to 125° C. for seven hours. At the end of the seven hour period, the reaction mass is cooled.

The reaction product contains the compounds having the structures:

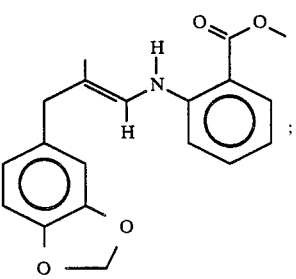

-continued

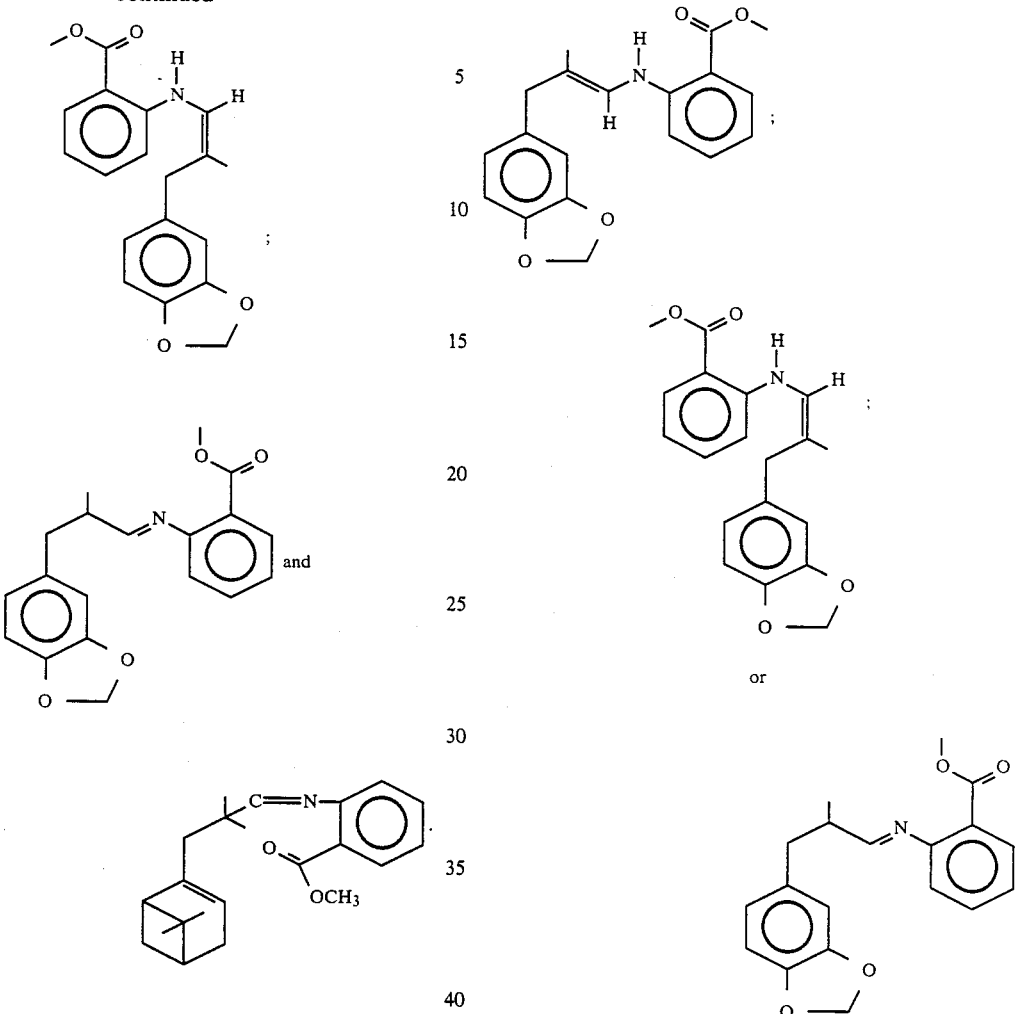

From a fragrance standpoint the resulting reaction product has a walnut, green, melony and ozoney aroma with floral, woody, animalic, walnut, green and ozoney topnotes.

FIG. 8 is the GC spectral scan for the resulting reaction product (Conditions: 50 m×0.32 mm OV-1 fuse silica column programmed at 225° C. isothermal).

FIG. 9 is the mass spectrum for the compound having the structure:

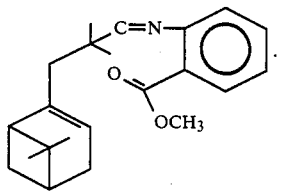

FIG. 10 is the mass spectrum for one of the compounds having one of the structures:

EXAMPLE III(B)

Preparation of Schiff Base Reaction Product of Methyl Anthranilate, Helional and Pinoisobutyraldehyde with the Mole Ratio of Pinoisobutyraldehyde:Helional:Methyl Anthranilate Being 1:2:3

A reation is in conditions the same as that of Example III(A) was carried out with the exception that the mole ratio of pinoisobutyraldehyde:helional:methyl anthranilate is 1:2:3.

The resulting reaction product from a fragrance standpoint has a green, floral, anisic, ozoney and fruity aroma with green, melony, ozoney, floral, anisic and animalic topnotes. From a flavor standpoint the resulting product has a lemony and oriental aroma and taste profile at 1 ppm.

EXAMPLE IV(A)

Preparation of Schiff Base of Methyl Anthranilate, Lyral and Helional with the Mole Ratio of Lyral:Helional:Methyl Anthranilate Being 2:1:3

Reaction:

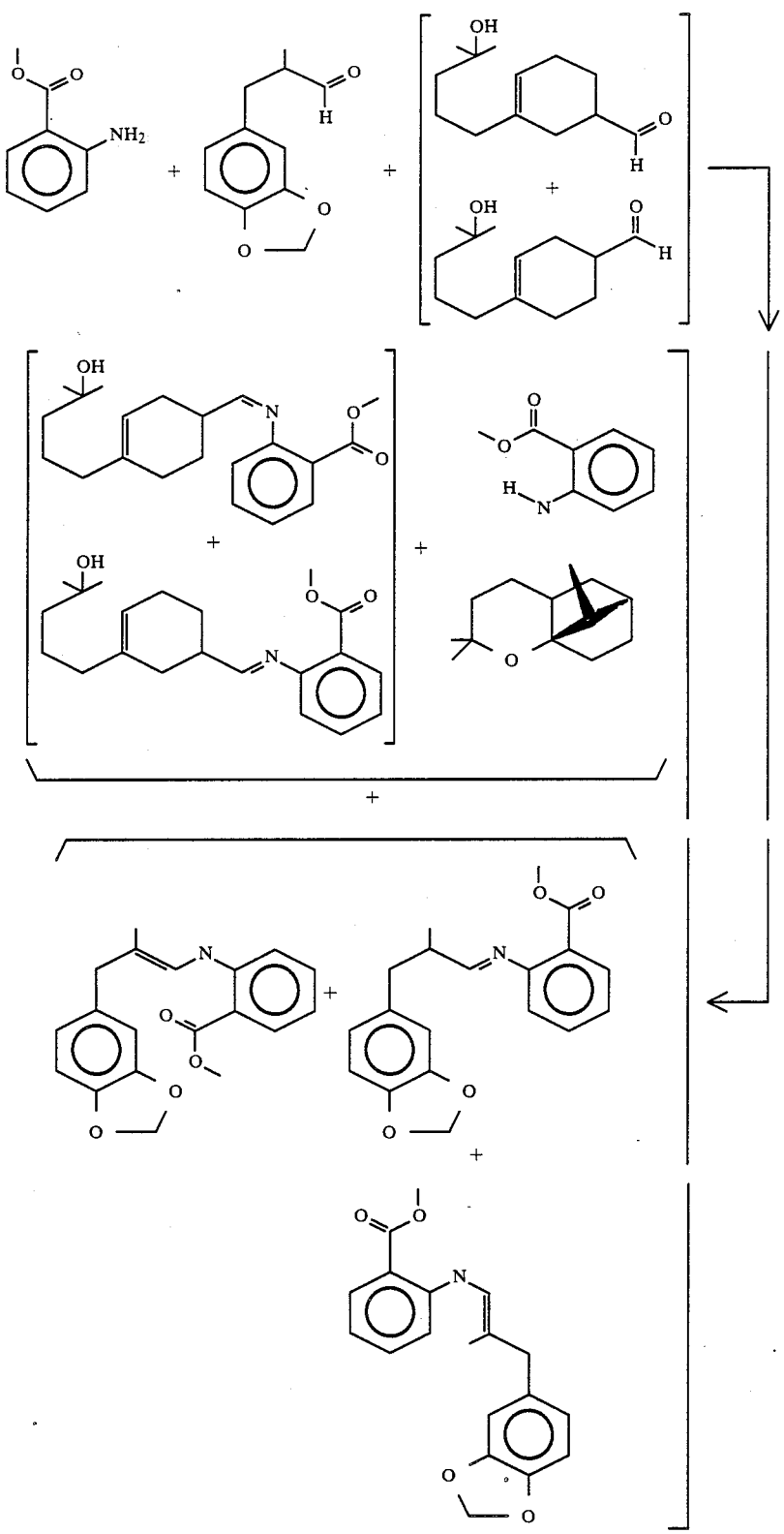

Into a 2 liter reaction flask equipped with vacuum apparatus and ice trap, mechanical stirrer, thermometer, fraction cutter and heating mantle is placed 453 grams of methyl anthranilate. The methyl anthranilate is heated to 50° C. Over a 15 minute period while maintaining the reaction mass at 50° C., 2 moles of lyral weighing 420 grams and one mole of helional weighting 192 grams is placed into the reaction vessel. The reaction mass is then closed and placed under 50 mm/Hg. vacuum and heated to 125° C. for a period of 7 hours.

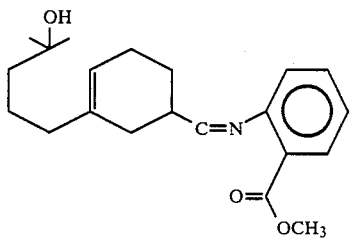

and

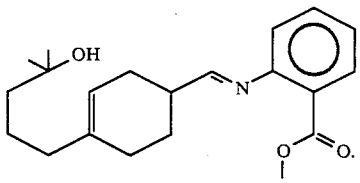

From a perfumery standpoint the resulting product has a green, floral and ozoney aroma with green, floral, ozoney and lemony topnotes.

From a flavor standpoint the resulting product has a concord grape and floral aroma and taste profile at 1 ppm.

FIG. 11 is the GC spectral scan for the resulting product (Conditions: 50 m×0.32 mm OV-1 fused silica column programmed at 225° C. isothermal).

FIGS. 12, 13, 14, 15, 16 and 17 are mass spectra of the various compounds (individually) produced as a result of the reaction in the instant example.

EXAMPLE IV(B)

Preparation of Schiff Base Reaction Productof Methyl Anthranilate, Helional and Lyral with the Mole Ratio of Lyral:Helional:Methyl Anthranilate Being 1:2:3

A reaction is carried out under conditions substantially identical to those of Example IV(A) with the exception that the mole ratio of lyral:helional:methyl anthranilate is 1:2:3.

From a perfumery standpoint the resulting product has a green, floral and ozoney aroma with grape and floral topnotes.

EXAMPLE V

Floral Perfume Compositions

The schiff base compositions of Examples II, III(A) and III(B) have melony, herbaceous, sweet, balsamic, walnut, green, ozoney and fruity aromas with piney, fruity, ozoney, floral, woody, animalic, walnut, green, melony and anisic topnotes. These materials have great warmth and richness and blend well with many floral concepts. Each of the schiff base compositions have rather unique floral notes of great value of perfumery. They may be demonstrated by the following floral fragrances whereby the schiff base compositions of Examples II, III(A) and III(B) are used to the extent of 5% by weight.

All three of these products perform quite well in fragrances and are judged to be very valuable fragrance materials:

TABLE II

| | | FLORAL FRAGRANCE | | |
|---|---|---|---|---|
| | | "V(A)" | "V(B)" | "V(C)" |
| | Citronellol | 12.3 | 12.3 | 12.3 |
| | Geraniol | 2.5 | 2.5 | 2.5 |
| | Amyl Cinnamic Aldehyde | 24.6 | 24.6 | 24.6 |
| | Galaxolide ®50 (Trademark for the Tricyclic Isochroman of International Flavors & Fragrances Inc.) | 9.8 | 9.8 | 9.8 |
| | Vertenex High Cis (Cis-t-Butylcyclohexenyl Acetate; Para Isomer) | 7.4 | 7.4 | 7.4 |
| | Rose Oxide | 0.7 | 0.7 | 0.7 |
| | Cinnamic Alcohol | 19.6 | 19.6 | 19.6 |
| | Aldehyde C-11 (n-Undecylenic Aldehyde) | 0.5 | 0.5 | 0.5 |
| | Aldehyde C-12 (n-Dodecyl Aldehyde in 10% solution in diethyl phthalate) | 0.5 | 0.5 | 0.5 |
| | Citronellal (10% solution in diethyl phthalate) | 0.5 | 0.5 | 0.5 |
| | Phenyl Ethyl Acetate | 2.5 | 2.5 | 2.5 |
| | Ylang Oil | 1.2 | 1.2 | 1.2 |
| | Indisan (Hydrogenated derivative of reaction product of Camphene and Resorcinol) | 3.7 | 3.7 | 3.7 |
| | Musk Ketone | 5.0 | 5.0 | 5.0 |
| | Oakmoss Resin | 0.5 | 0.5 | 0.5 |
| | Liatrix Absolute (10% in diethyl phthalate) | 2.5 | 2.5 | 2.5 |
| | Vetiver Acetate | 1.2 | 1.2 | 1.2 |
| | Diethyl Phthalate | 5.0 | 5.0 | 5.0 |
| | The schiff base reaction product of methyl anthranilate, helional and pino acetaldehyde of Example II. | 5.0 | 0 | 0 |
| | The Schiff base reaction product of methyl anthranilate, helional and pino isobutyraldehyde with the mole ratio of methyl anthranilate:helional:pino isobutyraldehyde being 1:1:2 produced according to Example III(A). | 0 | 5.0 | 0 |
| | The schiff base reaction product of methyl anthranilate, helional and pino isobutyraldehyde with the mole ratio of methyl anthranilate:helional: pino isobutyraldehyde being 1:2:3. | 0 | 0 | 5.0 |

The schiff base reaction product of Example II imparts to this floral fragrance melony, herbaceous, sweet, balsamic undertones with piney, fruity and ozoney topnotes. Accordingly, the fragrance can be described as "floral with a melony, herbaceous, sweet and balsamic undertone and piney, fruity and ozoney topnotes".

The schiff base composition of Example III(A) imparts to this floral formulation walnut, green, melony and ozoney undertones with floral, woody, animalic, walnut green and ozoney topnotes. Accordingly, the fragrance thus produced can be described as "floral with walnut, green, melony and ozoney undertones and floral, woody, animalic, walnut, green and ozoney topnotes".

The schiff base composition produced according to Example III(B) imparts to this floral formulation green, floral, anisic, ozoney and fruity undertones with green, melony, ozoney, floral, anisic and animalic topnotes.

Accordingly, the fragrance thus produced can be described as "floral with green, floral, anisic, ozoney and fruity undertones and green, melony, ozoney, floral, anisic and animalic topnotes".

EXAMPLE VI

Floral Perfume Compositions

The schiff base reaction product of lyral, methyl anthranilate and helional with the mole ratio of lyral:helional:methyl anthranilate being 2:1:3 produced according to Example IV(A) has a green, floral and ozoney aroma with green, floral, ozoney and lemony topnotes. The schiff base reaction product of lyral, helional and methyl anthranilate with the mole ratio of lyral:helional:methyl anthranilate being 1:2:3 has a green, floral and ozoney aroma with grape and floral topnotes. Each of these materials of Examples IV(A) and IV(B) have great warmth and richness and blend well with many floral concepts. They have rather unique floral notes of great value to perfumery.

The two of these products perform quite well in fragrances and are judged to be very valuable fragrance materials.

TABLE III

| Ingredients | FLORAL FRAGRANCE VI(A) | VI(B) |
|---|---|---|
| Citronellol | 12.3 | 12.3 |
| Geraniol | 2.5 | 2.5 |
| Amyl Cinnamic Aldehyde | 24.6 | 24.6 |
| Galaxolide ®50 (Trademark for the Tricyclic Isochroman of International Flavors & Fragrances Inc.) | 9.8 | 9.8 |
| Vertenex High Cis (Cis-t-Butylcyclohexenyl Acetate; Para Isomer) | 7.4 | 7.4 |
| Rose Oxide | 0.7 | 0.7 |
| Cinnamic Alcohol | 19.6 | 19.6 |
| Aldehyde C-11 (n-Undecylenic Aldehyde) | 0.5 | 0.5 |
| Aldehyde C-12 (n-Dodecyl Aldehyde in 10% solution in diethyl phthalate) | 0.5 | 0.5 |
| Citronellal (10% solution in diethyl phthalate) | 0.5 | 0.5 |
| Phenyl Ethyl Acetate | 2.5 | 2.5 |
| Ylang Oil | 1.2 | 1.2 |
| Indisan (Hydrogenated derivative of reaction product of Camphene and Resorcinol) | 3.7 | 3.7 |
| Musk Ketone | 5.0 | 5.0 |
| Oakmoss Resin | 0.5 | 0.5 |
| Liatrix Absolute (10% in diethyl phthalate) | 2.5 | 2.5 |
| Vetiver Acetate | 1.2 | 1.2 |
| Diethyl Phthalate | 5.0 | 5.0 |
| Schiff base reaction product of lyral:helional:methyl anthranilate with the mole ratio of lyral:helional:methyl anthranilate being 2:1:3 prepared according to Example IV(A). | 5.0 | 0 |
| Schiff base reaction product of lyral, helional and methyl anthranilate with the mole ratio of lyral:helional:methyl anthranilate being 1:2:3 prepared according to Example IV(B). | 0 | 5.0 |

The schiff base reaction product of lyral, helional and methyl anthranilate with the mole ratio of lyral:helional:methyl anthranilate being 2:1:3 prepared according to Example IV(A) imparts to this floral fragrance green, floral and ozoney undertones with green, floral, ozoney and lemony topnotes. Accordingly, the fragrance can be described as "floral with green, floral and ozoney undertones and green, floral, ozoney and lemony topnotes".

The schiff base reaction product of lyral, helional and methyl anthranilate with the mole ratio of lyral:helional:methyl anthranilate being 1:2:3 prepared according to Example IV(B) imparts to this floral formulation a green, floral and ozoney undertones with grape and floral topnotes. Accordingly, the fragrance thus produced can be described as "floral with green and ozoney undertones and grape topnotes".

EXAMPLE VII

Preparation of Cosmetic Powder Compositions

Cosmetic powder compositions are prepared by mixing in a ball mill 100 grams of talcum powder with 0.25 grams of each of the substances set forth in Table IV below. Each of the cosmetic powder compositions has an excellent aroma as described in Table IV below:

TABLE IV

| Substance | Aroma Description |
|---|---|
| The schiff base reaction product of helional and methyl anthranilate prepared according to Example I. | A green, orange flower fruity, ozoney and sweet, anisic aroma with grape, fruity, green, floral, anisic and ozoney topnotes. |
| The schiff base reaction product of methyl anthranilate, helional and pino acetaldehyde prepared according to Example II. | A melony, herbaceous sweet, balsamic aroma with piney, fruity and ozoney topnotes. |
| The schiff base reaction product of methyl anthranilate and helional and pino isobutyraldehyde with the mole ratio of pino isobutyraldehyde:helional:methyl anthranilate being 1:1:2. | A walnut, green, melony and ozoney aroma with floral, woody, animalic, walnut, green and ozoney topnotes. |
| The schiff base reaction product of methyl anthranilate, helional and pino isobutyraldehyde with the mole ratio of pino isobutyraldehyde:helional:methyl anthranilate being 1:2:3. | A green, floral, anisic, ozoney and fruity aroma with green, melony, ozoney, floral, anisic and animalic topnotes. |
| The schiff base reaction product of lyral, helional and methyl anthranilate with the mole ratio of lyral:helional:methyl anthranilate being 2:1:3 prepared according to Example IV(A). | A green, floral and ozoney aroma with green, floral, ozoney and lemony topnotes. |
| The schiff base reaction product of lyral, helional and methyl anthranilate with the mole ratio of lyral:helional:methyl anthranilate being 1:2:3 prepared according to Example IV(B) | A green, floral and ozoney aroma with grape and floral topnotes. |
| The perfume composition of Example V(A). | A floral with a melony herbaceous, sweet and balsamic undertone and piney, fruity and ozoney topnotes. |
| The perfume composition of Example V(B). | A floral with walnut green, melony and ozoney undertones and floral, woody, animalic, walnut, green and ozoney topnotes. |
| The perfume composition of Example V(C). | A floral with green, floral, anisic, ozoney and fruity undertones and green, melony, |

TABLE IV-continued

| Substance | Aroma Description |
|---|---|
| | ozoney, floral, anisic and animalic topnotes. |
| The perfume composition of Example VI(A). | A floral with green, floral and ozoney undertones and green, floral, ozoney and lemony topnotes. |
| The perfume composition of Example VI(B). | A floral with green and ozoney undertones and grape topnotes. |

EXAMPLE VIII

Perfumed Liquid Detergents

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table IV of Example VII are prepared containing 0.10%, 0.15%, 0.20%, 0.25%, 0.30% and 0.35% of the substance set forth in Table IV of Example VII. They are prepared by adding and homogeneously mixing the appropriate quantity of substance in Table IV of Example VII in the liquid detergent. The detergents all possess excellent aromas as set forth in Table VI of Example XIV, the intensity increasing with greater concentrations of substance as set forth in Table IV of Example VII.

EXAMPLE IX

Preparation of Colognes and Handkerchief Perfumes

Compositions as set forth in Table IV of Example VII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table IV of Example VII are imparted to the colognes and to the handkerchief perfumes at all levels indicated.

EXAMPLE X

Preparation of Soap Compositions

One hundred grams of soap chips (per sample) (IVORY ®, produced by the Procter & Gamble Company of Cincinnati, Ohio), are each mixed with one gram sample of substances as set forth in Table IV of Example VII until homogeneous compositions are obtained. In each of the cases, the homogeneous compositions are heated under 8 atmospheres pressure at 180° C. for a period of three hours and the resulting liquid are placed into soap molds. The resulting soap cakes, on cooling, manifest aromas as set forth in Table IV of Example VII.

EXAMPLE XI

Preparation of Solid Detergent Compositions

Detergents are prepared using the following ingredients according to Example I of Canadian Pat. No. 1,007,948 (incorporated herein by reference):

| Ingredient | Percent by Weight |
|---|---|
| NEODOL ®45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table IV of Example VII. Each of the detergent samples has an excellent aroma as indicated in Table IV of Example VII.

EXAMPLE XII

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.);
   57% $C_{20-22}$ HAPS
   22% isopropyl alcohol
   20% antistatic agent
   1% of one of the substances as set forth in Table IV of Example VII.

Fabric softening compositions prepared according to Example I at column 15 of U.S. Pat. No. 3,632,396 having aroma characteristics as set forth in Table IV of Example VII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table IV of Example VII is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table IV of Example VII, supra.

EXAMPLE XIII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of polymer is dissolved in the alcohol. The following ingredients are added to the PVP/VA alcoholic solution:

| Ingredients | Weight Percent |
|---|---|
| Dioctyl sebacate | 0.05 |
| Benzyl alcohol | 0.10 |
| Dow Corning 473 fluid | 0.10 |

-continued

| Ingredients | Weight Percent |
|---|---|
| (prepared by the Dow Corning Corporation) | |
| Tween 20 surfactant (prepared by ICI America Corporation) | 0.03 |
| One of the perfumery substances as set forth in Table IV of Example VII, supra. | 0.10 |

The perfume substances as set forth in Table IV of Example VII add aroma characteristics as set forth in Table IV of Example VII which are rather intense and aesthetically pleasing to the users of the soft-feel, good-hold pump hair sprays.

EXAMPLE XIV

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table IV of Example VII is added to the mixture. The resulting mixture is cooled to 40° C. and blending is carried out for an additional one hour in each case. At the end of the blending period, the resulting material has a pleasant fragrance as indicated in Table IV of Example VII.

EXAMPLE XV

Each of the fragrance materials of Table IV of Example VII, supra, are added to a 50:50 weight:weight mixture of low density polyethylene:polyepsilon caprolactone PCL-700 forming pellets with scents as set forth in Table IV of Example VII, supra.

75 Pounds of a 50:50 mixture of PCL-700 polyepsilon caprolactone (manufactured by the Union Carbide Corporation of New York, N.Y. having a melting point of about 180°-190° F.):Low density polyethylene, are heated to about 250° F. in a container of the kind illustrated in FIGS. 20 and 21. 25 Pounds of each of the fragrance materials as set forth in Table IV of Example VII, is then quickly added to the liquified polymer mixture, the lid 228 is put in place and the agitating means 273 are actuated. The temperature is then raised to about 260° F. and the mixing is continued for 5-15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table IV of Example VII, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table IV of Example VII, supra. The sheets of films are cut into strips of 0.25" in width × 3" in length and placed into room air fresheners.

On operation of the room air freshener, after four minutes, the room in each case has an aesthetically pleasing aroma with no foul odor being present, the aroma being described in Table IV of Example VII, supra.

EXAMPLE XVI

Citrus/Grape Flavor Formulations

The following citrus/grape flavor formulations are prepared:

| Ingredients | Parts by Weight | | |
|---|---|---|---|
| | XVI(A) | XVI(B) | VI(C) |
| The schiff base reaction product of pino acetaldehyde, helional and methyl anthranilate prepared according to Example II. | 26.0 | 0 | 13.0 |
| The schiff base reaction product of Example IV(A), the Schiff base reaction product of helional, lyral and methyl anthranilate with the mole ratio of helional:lyral: methyl anthranilate being 1:2:3. | 0 | 26.0 | 13.0 |
| Natural Lemon Oil Terpeneless | 10.0 | 10.0 | 10.0 |
| Acetaldehyde | 0.6 | 0.6 | 0.6 |
| Alpha-Terpineol | 2.1 | 2.1 | 2.1 |
| Citral | 1.8 | 1.8 | 1.8 |
| Carvone | 0.24 | 0.24 | 0.24 |
| Terpinolene | 1.2 | 1.2 | 1.2 |
| Alpha-Terpinene | 0.25 | 0.25 | 0.25 |
| Diphenyl | 0.25 | 0.25 | 0.25 |
| Alpha-Fenchyl Alcohol | 0.25 | 0.25 | 0.25 |
| Limonene | 0.35 | 0.35 | 0.35 |
| Linalool | 0.25 | 0.25 | 0.25 |
| Geranyl Acetate | 0.25 | 0.25 | 0.25 |
| Nootkatone | 0.25 | 0.25 | 0.25 |
| Neryl Acetate | 0.25 | 0.25 | 0.25 |
| Cyclohexyldisulfide | 2.5 | 0 | 2.5 |

The flavor formulation of Example "A" (hereinafter referred to as Example XVI(A) has an intense citrusy and "natural" grape aroma and taste profile.

The flavor formulation of Example XVI(B) has an intense citrusy "natural lemon" aroma and taste profile due to the presence of the schiff base reaction product of helional, lyral and methyl anthranilate.

The flavor formulation of Example XVI(C) has a "natural" grape and lemony aroma profile with the lemon nuances augmenting and enhancing the grape nuances and this is primarily due to the presence of the mixture of the schiff base reaction product of lyral, helional and methyl anthranilate of Example IV(A) and of the schiff base reaction product of helional, pino acetaldehyde and methyl anthranilate of Example II.

EXAMPLE XVII

A. Powder Flavor Compositions

20 Grams of each of the flavor compositions of Examples XVI(A), XVI(B) and XVI(C) containing schiff base reaction products of methyl anthranilate with helional and pino acetaldehyde and/or lyral is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B. Sustained Release Flavors

The following mixtures are prepared:

| Ingredients | Parts by Weight |
| --- | --- |
| Liquid Citrus/Grape Flavor Compositions of one of Examples XVI(A), XVI(B) or XVI(C). | 20.0 |
| Propylene glycol | 9.0 |
| CAB-O-SIL ®M-5 Brand of Silica produced by the Cabot Corporation of 125 High Street, Boston, Massachusetts 02110: Physical Properties: Surface area: 200 m²/gm Nominal particle size: 0.012 microns Density: 2.3 lbs./cu.ft. | 5.0 |

The Cab-O-Sil is dispersed in each of the liquid citrus/grape flavor compositions of Examples XVI(A), XVI(B) and XVI(C) with vigorous stirring, thereby resulting in a viscous liquid. 71 Parts by weight of each of the powder flavor compositions of Part A, supra, is then blended into the said viscous liquids, with stirring at 25° C. for a period of 30 minutes resulting in dry free flowing sustained release flavor powders.

EXAMPLE XVIII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of each of the liquid flavor compositions of Examples XVI(A), XVI(B) and XVI(C) are separately added to the solution which is then homogenized to form an emulsion having particle size in the range of 5–40 microns. The material is kept at 120° F. under which conditions the gelatin will not gel.

Coacervation is induced by adding, slowly and uniformly 40 parts by weight of a 20% aqueous solution of sodium sulphate. During coacervation the gelatin molecules are deposited uniformly about each oil droplet as a nucleus.

Gelatin is effected by pouring the heated coacervate mixture into 1,000 parts by weight of 7% aqueous solution of sodium sulfate at 65° C. The resulting gelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XIX

Chewing Gums

100 Parts by weight of chicle are mixed with 4 parts by weight of each of the flavors prepared in accordance with Example XVII(B). 300 Parts of sucrose and 100 parts of corn syrup are added. Mixing is effected in a ribbon blender with jacketed side walls of the type manufactured by the Baker Perkins Company.

The resultant chewing gum is then manufactured into strips 1 inch in width and 0.1 inches in thickness. The strips are cut into lengths of 3 inches each. On chewing, the chewing gum has a pleasant, long lasting citrus/grape flavor.

EXAMPLE XX

Chewing Gums

100 Parts by weight of chicle are mixed with 18 parts by weight of each of the flavors prepared in accordance with Example XVIII. 300 Parts of sucrose and 100 parts of corn syrup are then added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long lasting citrus/grape flavor.

EXAMPLE XX

Toothpaste Formulations

The following separate groups of ingredients are prepared:

| Parts by Weight | Ingredients |
| --- | --- |
| Group "A" | |
| 30.200 | Glycerine |
| 15.325 | Distilled Water |
| 0.100 | Sodiium Benzoate |
| 0.125 | Saccharin Sodium |
| 0.400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N—Lauroyl Sarcosinate (foaming agent) |
| Group "D" | |
| 1.200 | Each of the Flavor Materials of Example XVII(B). |

Procedure

1. The ingredients in Group "A" are stirred and heated in a steam jacketed kettle to 160° F.;
2. Stirring is continued for an additional three to five minutes to form a homogeneous gel;
3. The powders of Group "B" are added to the gel, while mixing, until a homogeneous paste is formed;
4. With stirring, the flavor of "D" is added and lastly the sodium n-lauroyl sarcosinate;
5. The resultant slurry is then blended for one hour. The completed paste is then transferred to a three roller mill and then homogenized, and finally tubed.

The resulting toothpaste when used in a normal tooth brushing procedure yields a pleasant citrus/grape flavor, of constant strong intensity throughout said procedure (1-1.5 minutes).

EXAMPLE XXI

Chewable Vitamin Tablets

Each of the flavor materials produced according to the process of Example XVII(B) is added to a Chewable Vitamin Tablet Formulation at a rate of 10 gm/Kg which chewable vitamin tablet formultion is prepared as follows:

In a Hobart Mixer the following materials are blended to homogeneity:

|  | Gms/1000 Tablets |
|---|---|
| Vitamin C (ascorbic acid) as ascorbic acid-sodium ascorbate mixture 1:1 | 70.00 |
| Vitamin B$_1$ (thiamine mononitrate) as ROCOAT ® thiamine mononitrate 33⅓% (Hoffman La Roche) | 4.0 |
| Vitamin B$_2$ (riboflavin) as ROCOAT ® riboflavin 33⅓% | 5.0 |
| Vitamin B$_6$ (pyridoxine hydrochloride) as ROCOAT ® pyridoxine hydrochloride 33⅓% | 4.0 |
| Niacinamide as ROCOAT ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% ROCHE ® | 6.6 |
| d-Biotin | 0.044 |
| Each of the flavor formulations of Example XVII(B) | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong citrus/grape flavor for a period of 12 minutes.

EXAMPLE XXII

Chewing Tobacco

Onto 100 pounds of tobacco for chewing (85% Wisconsin lead and 15% Pennsylvania leaf) the following casing is sprayed at a rate of 30%:

| Ingredients | Parts by Weight |
|---|---|
| Corn Syrup | 60.0 |
| Licorice | 10.0 |
| Glycerin | 20.0 |
| Fig Juice | 4.6 |
| Prune Juice | 5.0 |
| Each of the Flavor Materials of Example XVII(B) | 0.4 |

The resultant product is redried to a moisture content of 20%. On chewing, this tobacco has an excellent substantially consistent, long-lasting citrus/grape and licorice aroma and taste profile in conjunction with the tobacco note.

EXAMPLE XXIII

To 100 parts by weight of GOYA ® mango nectar (produced by the Goya Corporation of New York, N.Y.) is added 10 ppm of the schiff base reaction product of Example III(B), the schiff base reaction product of helional, pino isobutyraldehyde and methyl anthranilate with the mole ratio of pino isobutyraldehyde:helional:methyl anthranilate being 1:2:3. The resulting schiff base reaction product adds to the mango nectar a very natural lemony which causes the resulting mango nectar to be aesthetically pleasing and to a 25 member panel to be preferred over the standard mango nectar.

EXAMPLE XXIV

A fabric washing deodorant detergent powder product is prepared by admixing the following ingredients:

| Ingredients | Parts by Weight |
|---|---|
| Linear alkylbenzene sulfonate | 9.0 |
| C$_{13}$-C$_{15}$ straight chain alcohols (30:30:40 mixture of C$_{13}$, C$_{14}$, and C$_{15}$ straight chain alcohol) | 4.0 |
| Sodium tripolyphosphate | 16.0 |
| ZEAOLIGHT | 8.0 |
| Sodium silicate | 4.0 |
| Magnesium silicate | 0.8 |
| Ethylene diamine | 0.6 |
| N,N,N',N'—[tetra(methylene phosphonic acid)] sodium carboxy methyl cellulose | 0.9 |
| Anti-foam | 1.5 |
| Sodium Perborate tetrahydrate | 14.0 |
| N,N,N',N'—Tetraacetyl Glycoluril | 4.2 |
| Schiff base reaction product of helional and methyl anthranilate produced according to Example I. | 0.35 |
| Water | 45.0 |
| Sodium sulfate | 5.0 |

The resulting fabric washing deodorant detergent powder on use gives rise to a very pleasant "fresh air" aroma without any aesthetically displeasing aromas subsequent to the washing of the fabrics in the standard washing machine cycle.

When the foregoing composition is created wherein the helional-methyl anthranilate schiff base is replaced in the same quantity by any of the following schiff bases, identical results are achieved:

(i) The schiff base reaction product of methyl anthranilate, helional and pino acetaldehyde prepared according to Example II;

(ii) The schiff base reaction product of methyl anthranilate, helional and pino isobutyraldehyde prepared according to Example III(A);

(iii) The schiff base reaction product of methyl anthranilate, helional and pino isobutyraldehyde prepared according to Example III(B);

(iv) The schiff base reaction product of lyral, helional and methyl anthranilate prepared according to Example IV(A); and (v) The schiff base reaction product of lyral, helional and methyl anthranilate prepared according to Example IV(B).

Deodorant detergent products have also been prepared according to Examples I-IX of U.S. Pat. No. 4,304,679 incorporated by reference herein.

Thus, exemplified herein by reference are the following deodorant detergent products comprising:

(i) from 0.5 to 99.99% by weight of a non-soap detergent active compound; and (ii) from 0.01 to 10% by weight of a deodorant composition comprising from 45 to 100% by weight of at least one of the schiff bases or schiff base compositions exemplified by Examples I-IV(B), supra, said schiff base components having a lipoxidase-inhibiting capacity of at least 50% or a Raoult variance ratio of at least 1.1 as stated in said U.S. Pat. No. 4,304,679, with the schiff base composition having a deodorant value of from 0.5 to 3.5 as measured by the deodorant value test as specifically set forth in said U.S. Pat. No. 4,304,679 and exemplified therein.

Furthermore, the examples of U.S. Pat. No. 4,663,068 are also incorporated herein by reference.

Thus, exemplified herein are detergent powder products suitable for the washing of fabrics comprising:

(i) from 5 to 40% by weight of a non-soap detergent active compound comprising an anionic detergent active compound;

(ii) from 1 to 90% of a non-soap detergency builder;

(iii) from 1 to 30% by weight a peroxy bleach compound together with an activator therefor;

(iv) from 0.1 up to 10% by weight of a bleach stable perfume which comprises 50-100% by weight of a bleach stable schiff base component as exemplified by any one of Examples I-IX or mixtures thereof, having a Lipoxidase-inhibiting capacity of at least 50% or a Raoult variance ratio of at least 1.1 as defined according U.S. Pat. No. 4,663,068 incorporated by reference herein, with the schiff base reaction product as defined in any one of Examples I-IV(B), supra being stable in the presence of sodium perborate tetrahydrate or any other alkali metal perborate tetrahydrate and N,N,N',N'-tetraacetyl ethylenediamine (TEAD) according to the bleach stability test as defined in said U.S. Pat. No. 4,663,068 incorporated by reference herein, the bleach stable deodorant schiff base having a Malodor Reduction Value of from 0.25 up to 3.0 as measured by the Malodor Reduction Value test defined in said U.S. Pat. No. 4,663,068 incorporated by reference herein.

The peroxy bleach activator may be exemplified by the following peroxy bleach activators:
N,N,N',N'-tetracetyl ethylenediamine;
N,N,N',N'-tetracetyl glycoluril;
Glucose pentaacetate;
Sodium acetoxybenzene sulphonate;
Sodium nonanoyloxybenzene sulphonate;
Sodium octanoyloxybenzene sulphonate; and
mixtures thereof.

The non-soap anionic detergent active compound may be selected from the group consisting of sodium and potassium alkyl sulphates, sodium potassium and ammonium alkyl benzene sulphonates, sodium alkyl glyceryl ether sulphates, sodium coconut oil fatty acids monoglyceride sulphates and sulphonates, sodium and potassium salts of sulphuric acid esters of higher ($C_9$-$C_{18}$) fatty alcohol-alkylene oxide, the reaction products of fatty acids esterified with isethionic acid and neutralized with sodium hydroxide, sodium and potassium salts of fatty acid amides of methyl taurine, alkane monosulphonates, olefin sulphonates and mixtures thereof.

The nonionic detergent active compound may be selected from the group consisting of reaction products of alkylene oxides with alkyl ($C_6$-$C_{22}$) phenols, the condensation products of aliphatic ($C_8$-$C_{18}$) primary or secondary linear or branched alcohols with ethylene oxide, products made by condensation of ethylene oxide with the reaction products of propylene oxide and ethylene diamine, long-chain tertiary amine oxides, long-chain phosphine oxides and dialkyl sulphoxides and mixtures thereof.

What is claimed is:

1. A schiff base reaction product produced according to the process of reacting an alkyl anthranilate having the structure:

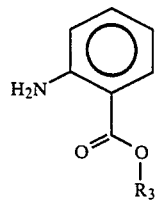

wherein $R_3$ is methyl or ethyl with helional having the structure:

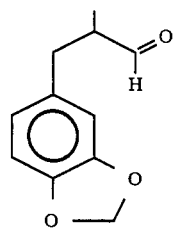

and an aldehyde having the structure:

wherein the aldehyde having the structure:

is selected from the group consisting of:
(a) Pinoacetaldehyde having the structure:

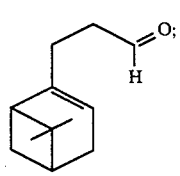

(b) Pinoisobutyraldehyde having the structure:

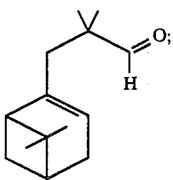

and (c) Lyral, a mixture of compounds having the structures:

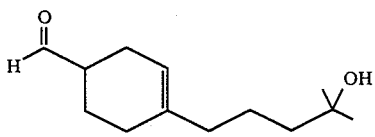

and

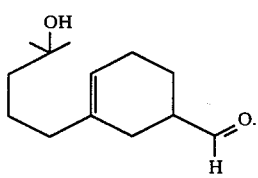

2. The schiff base reaction product of claim 1 wherein the aldehyde having the structure:

is pinoacetaldehyde having the structure:

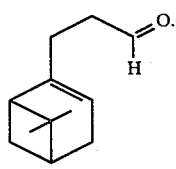

3. The schiff base reaction product of claim 1 wherein the aldehyde having the structure:

is pinoisobutyraldehyde having the structure:

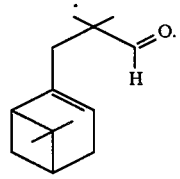

4. The schiff base reaction product of claim 1 wherein the aldehyde is lyral, a mixture of compounds having the structures:

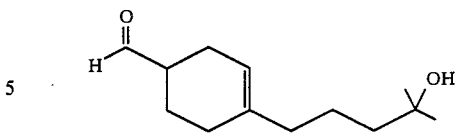

and

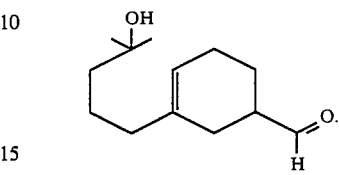

5. A process for augmenting or enhancing the aroma or taste of consumable material selected from the group consisting of perfume compositions, perfumed articles, colognes, perfumed polymers, foodstuffs, chewing gums, toothpastes, medicinal products and chewing tobaccos comprising the step of intimately admixing with said consumable material, an aroma or taste augmenting or enhancing quantity of at least one schiff base reactionn product produced according to claim 1.

6. A process for augmenting or enhancing the aroma or taste of consumable material selected from the group consisting of perfume compositions, perfumed articles, colognes, perfumed polymers, foodstuffs, chewing gums, toothpastes, medicinal products and chewing tobaccos comprising the step of intimately admixing with said consumable material, an aroma or taste augmenting or enhancing quantity of at least one schiff base reaction product produced according to claim 2.

7. A process for augmenting or enhancing the aroma or taste of consumable material selected from the group consisting of perfume compositions, perfumed articles, colognes, perfumed polymers, foodstuffs, chewing gums, toothpastes, medicinal products and chewing tobaccos comprising the step of intimately admixing with said consumable material, an aroma or taste augmenting or enhancing quantity of at least one schiff base reaction product produced according to claim 3.

8. A process for augmenting or enhancing the aroma or taste of consumable material selected from the group consisting of perfume compositions, perfumed articles, colognes, perfumed polymers, foodstuffs, chewing gums, toothpastes, medicinal products and chewing tobaccos comprising the step of intimately admixing with said consumable material, an aroma or taste augmenting or enhancing quantity of at least one schiff base reaction product produced according to claim 4.

9. The process of claim 5 wherein the consumable material is a perfumed article and the perfumed article is a solid or liquid anionic, cationic, nonionic or zwitterionic detergent.

10. The process of claim 5 wherein the consumable material is a perfumed article and the perfumed article is a fabric softener composition or drier-added fabric softener article.

11. The process of claim 5 wherein the consumable material is a perfume composition or cologne.

12. The process of claim 5 wherein the consumable material is a perfumed polymer.

13. The process of claim 5 wherein the consumable material is a foodstuff or chewing gum.

14. The process of claim 5 wherein the consumable material is a medicinal product.

15. The process of claim 5 wherein the consumable material is a chewing tobacco.

16. A detergent powder product suitable for use in the washing of fabrics which comprises:
   (i) from 5 to 40% by weight of a non-soap detergent active compound comprising an anionic detergent active compound;
   (ii) from 1 to 90% by weight of a non-soap detergency builder;
   (iii) from 1 to 30% by weight of a peroxy bleach compound together with an activator therefor;
   (iv) from 0.1 up to 5% of a bleach stable perfume which comprises 50 to 100% of at least one schiff base reaction product defined according to claim 1 having a lipoxidase inhibiting capacity of at least 50% or a Raoult variance ratio of at least 1.1 wherein the schiff base reaction product or mixture of schiff base reaction products are judged to be stable in the presence of sodium perborate tetrahydrate and N,N,N',N'-tetraacetyl ethylenediame (TEAD) according to the bleach stability test, said schiff base reaction product or mixture of schiff base reaction products having a malodor reduction value of from 0.25 to 3 as measured by the malodor reduction value test.

17. A deodorant detergent product comprising:
   (i) from 0.5 to 99.99% by weight of a non-soap detergent active compound; and
   (ii) from 0.1 to 10% by weight of a deodorant composition comprising from 45 to 100% by weight of at least one schiff base reaction product defined according to claim 1, said schiff base reaction product having a lipoxidase-inhibiting capacity of at least 50% or a Raoult variance ratio of at least 1.1 with the schiff base having a deodorant value of from 0.50 up to 3.5 as measured by the deodorant value test.

* * * * *